(12) United States Patent
Rex et al.

(10) Patent No.: US 8,977,024 B1
(45) Date of Patent: Mar. 10, 2015

(54) DISTRIBUTED ANATOMICAL IMAGE ANALYSIS

(71) Applicant: Afraxis, Inc., La Jolla, CA (US)

(72) Inventors: Christopher Steven Rex, San Diego, CA (US); Steven Ray Boikess, San Diego, CA (US)

(73) Assignee: Afraxis, Inc., La Jolla, CA (US)

( * ) Notice: Subject to any disclaimer, the term of this patent is extended or adjusted under 35 U.S.C. 154(b) by 0 days.

(21) Appl. No.: 14/170,469

(22) Filed: Jan. 31, 2014

(51) Int. Cl.
*G06K 9/00* (2006.01)
*G06T 7/00* (2006.01)

(52) U.S. Cl.
CPC .................................. *G06T 7/0012* (2013.01)
USPC ......................................................... 382/128

(58) Field of Classification Search
None
See application file for complete search history.

(56) References Cited

U.S. PATENT DOCUMENTS

| | | | |
|---|---|---|---|
| 7,761,240 B2* | 7/2010 | Saidi et al. | 702/19 |
| 8,023,714 B2* | 9/2011 | Soenksen | 382/132 |
| 8,150,192 B2* | 4/2012 | Niemeyer et al. | 382/256 |
| 2003/0013951 A1* | 1/2003 | Stefanescu et al. | 600/407 |
| 2006/0159325 A1* | 7/2006 | Zeineh et al. | 382/128 |
| 2008/0162352 A1 | 7/2008 | Gizewski | |
| 2008/0267481 A1* | 10/2008 | Nakamura | 382/131 |
| 2008/0306980 A1* | 12/2008 | Brunner et al. | 707/102 |
| 2009/0204436 A1* | 8/2009 | Thorne et al. | 705/3 |
| 2009/0213214 A1* | 8/2009 | Yamada | 348/80 |
| 2009/0290768 A1* | 11/2009 | De La Torre-Bueno | 382/128 |
| 2010/0111396 A1* | 5/2010 | Boucheron | 382/133 |
| 2010/0254589 A1* | 10/2010 | Gallagher | 382/133 |
| 2010/0266184 A1* | 10/2010 | Kitamura | 382/131 |
| 2011/0176710 A1* | 7/2011 | Mattiuzzi et al. | 382/128 |
| 2011/0216953 A1 | 9/2011 | Callahan et al. | |
| 2011/0257507 A1* | 10/2011 | Gregory et al. | 600/410 |
| 2012/0008838 A1* | 1/2012 | Guyon et al. | 382/128 |
| 2013/0250144 A1* | 9/2013 | Takayama | 348/239 |
| 2014/0037162 A1* | 2/2014 | Papier et al. | 382/128 |
| 2014/0063194 A1* | 3/2014 | Zhuang et al. | 348/46 |

* cited by examiner

*Primary Examiner* — Shervin Nakhjavan
(74) *Attorney, Agent, or Firm* — Wilson Sonsini Goodrich & Rosati

(57) ABSTRACT

Disclosed are platforms, systems, computer program products for high throughput, distributed screening and analysis of images by a plurality of human image analysts, including methods of using the same.

29 Claims, 17 Drawing Sheets

Fig. 5
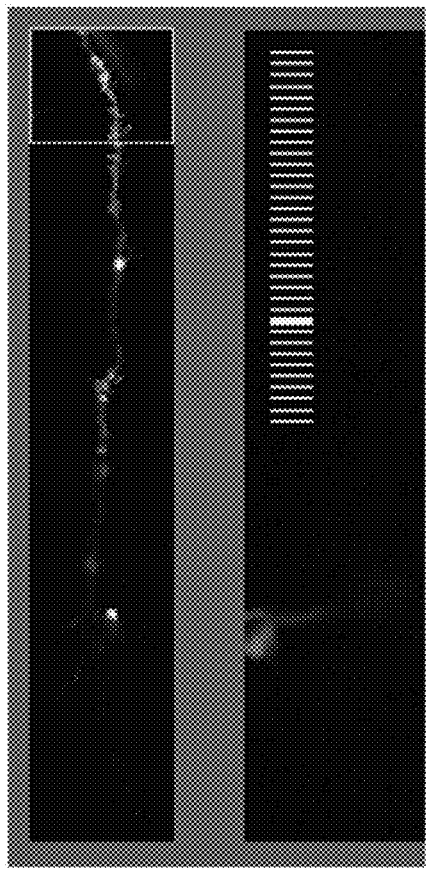 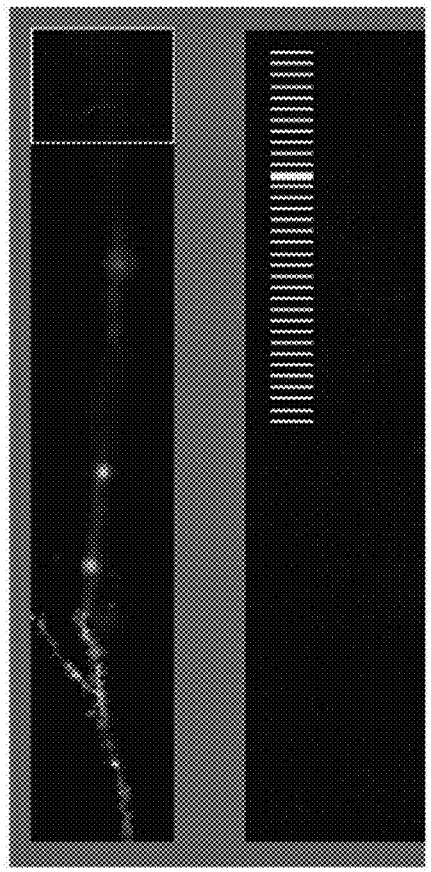
Initial Z-Position　　　　　　　　　Moving Down Dendrite

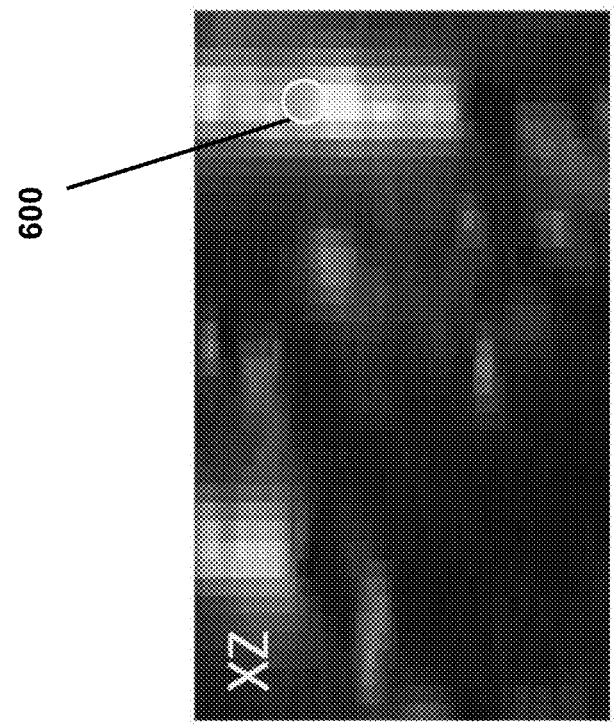
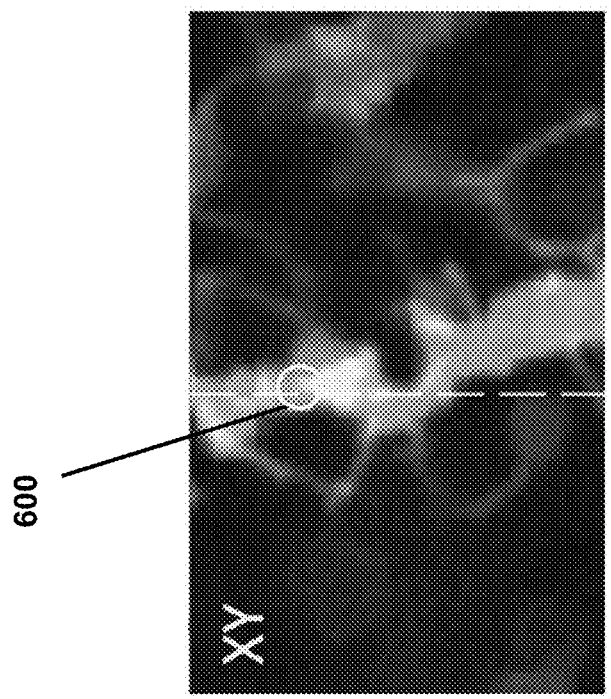
Fig. 6

1400  1410

1400  1410  1500

DISTRIBUTED ANATOMICAL IMAGE ANALYSIS

BACKGROUND OF THE INVENTION

In central nervous system (CNS) drug discovery, candidate compounds must be evaluated for safety and efficacy. Traditionally, behavioral models are used to evaluate efficacy and detect unwanted CNS effects. However, traditional behavioral measures are associated with artifacts.

SUMMARY OF THE INVENTION

Neural networks are comprised of dense, complex networks of synapses. Dendritic spines form the basis of neural networks of synapses and mediate learning, memory, and cognition. Spine morphology reflects synaptic strength and underlies synaptic plasticity. Dendritic spine abnormalities are thought to underlie many CNS disorders. In fact, spine deficits in in vitro and animal disease models mimic humans.

Dendritic spine analysis has been applied to CNS drug discovery to evaluate efficacy and unwanted CNS effects. However, automated software processes are inadequate. Anatomical images are not ideal and, in most cases, contain numerous artifacts that confound automated image analysis systems. Software agents fail to adequately identify the subtle differences in neuroanatomy that indicate a particular diagnosis or therapeutic effect. Moreover, attempts to perform manual analysis of dendritic spine morphology are of limited value due to slow, low throughput processes and artifacts introduced by differences in subjective interpretation across individual analysts.

Described herein are platforms, systems, media, and methods for distributed image analysis that facilitate dendritic spine quantification that is faster and more informative than preclinical behavioral models. The technologies described herein also provide marked improvements over both fully automated and manual forms of dendritic spine analysis. Advantages of the platforms, systems, media, and methods described herein include, but are not limited to, elimination of artifacts associated with traditional behavioral measures, statistical identification of aberrant analyst practices, interpretations, and measurements, high throughput image processing, complete scalability, and application across species, dosing regimens, and methodologies. In some embodiments, the advantages further include the ability to reliably evaluate greater than ½ million dendritic spines per month. In some embodiments, the advantages further include allowing analysts with minimal training to rapidly and effectively perform dendritic spine quantification.

In one aspect, disclosed herein are computer-based platforms comprising: a plurality of computers, each computer configured to provide an image analyst application, the application operated by a human image analyst, the application comprising: a software module configured to receive an anatomical image; and a software module configured to provide an interface for identifying and marking a morphological feature of the image; and a server configured to provide a management application comprising: a software module configured to distribute the anatomical image to a plurality of the image analyst applications; a software module configured to receive marked images from the analyst applications and calculate a score for each image, the score based on the marking; and a software module configured to statistically compare the scores to identify aberrant image analyst practices or image interpretations. In some embodiments, the anatomical image is distributed to about 10, about 5, or about 2 image analyst applications. In some embodiments, the anatomical image is a two-dimensional, three-dimensional, or four-dimensional image. In further embodiments, the anatomical image comprises a plurality of two-dimensional images in a Z-axis to create a three-dimensional image. In further embodiments, the anatomical image comprises a plurality of three-dimensional images representing a time progression to create a four-dimensional image. In some embodiments, the anatomical image is a histopathology image. In some embodiments, the anatomical image is of a neural sample. In some embodiments, the anatomical image is a confocal micrograph. In some embodiments, the marking comprises making a measurement of the morphological feature. In some embodiments, the score is used for diagnosis of medical conditions or evaluation of pharmacological therapies. In some embodiments, the morphological feature is a feature of a dendrite or a dendritic spine. In some embodiments, the measurement comprises a density, a diameter, a length, or a combination thereof. In some embodiments, the measurement comprises a dendritic spine density, a dendritic spine head diameter, a dendritic spine length, a dendritic spine neck diameter, a dendritic spine distance from a dendrite soma, a dendrite diameter, or a combination thereof. In some embodiments, the management application further comprises a database of anatomical images and associated scores.

In another aspect, disclosed herein are non-transitory computer-readable storage media encoded with a computer program including instructions executable by a processor to create a distributed image analysis application comprising: a software module configured to receive a two-, three-, or four-dimensional anatomical image from a centralized server, the anatomical image provided to a plurality of image analysis applications; a software module configured to provide an interface for viewing the image in three-dimensions, the interface for viewing the image comprising tools for manipulating the image in X and Y axes, and optionally, Z axis, and optionally, time progression; a software module configured to provide an interface for identifying and marking a morphological feature of the image; a software module configured to provide an interface for identifying and marking a morphological sub-feature of the image; and a software module configured to transmit the marked image to the centralized server; provided that the application is adapted for operation by a human image analyst. In some embodiments, the application is adapted for rapid throughput image analysis. In some embodiments, the anatomical image is provided to about 10, about 5, or about 2 image analyst applications. In some embodiments, the anatomical image comprises a plurality of two-dimensional images in a Z-axis to create a three-dimensional image. In some embodiments, the anatomical image comprises a plurality of three-dimensional images representing a time progression to create a four-dimensional image. In some embodiments, the anatomical image is a histopathology image. In some embodiments, the anatomical image is of a neural sample. In some embodiments, the anatomical image is a confocal micrograph. In some embodiments, the marking comprises making a measurement of the morphological feature or sub-feature. In some embodiments, the score is used for diagnosis of medical conditions or evaluation of pharmacological therapies. In some embodiments, the morphological feature is a feature of a dendrite. In some embodiments, the morphological sub-feature is a feature of a dendritic spine. In some embodiments, the measurement comprises a density, a diameter, a length, or a combination thereof. In some embodiments, the measurement comprises a dendritic spine density, a dendritic spine head diameter, a dendritic spine length, a dendritic spine neck diameter, a dendritic spine distance from a dendrite soma, a dendrite diameter, or a combination thereof. In some embodiments, the application further comprises a database of anatomical images and associated scores.

In another aspect, disclosed herein are computer-implemented systems comprising: a digital processing device comprising an operating system configured to perform executable instructions and a memory device; and a computer program including instructions executable by the digital processing device to create a distributed image analysis application comprising: a software module configured to receive a two-, three-, or four-dimensional anatomical image from a centralized server, the anatomical image provided to a plurality of image analysis applications; a software module configured to provide an interface for viewing the image in three-dimensions, the interface for viewing the image comprising tools for manipulating the image in X and Y axes, and optionally, Z axis, and optionally, time progression; a software module configured to provide an interface for identifying and marking a morphological feature of the image; a software module configured to provide an interface for identifying and marking a morphological sub-feature of the image; and a software module configured to transmit the marked image to the centralized server; provided that the application is adapted for operation by a human image analyst. In some embodiments, the application is adapted for rapid throughput image analysis. In some embodiments, the anatomical image is provided to about 10, about 5, or about 2 image analyst applications. In some embodiments, the anatomical image comprises a plurality of two-dimensional images in a Z-axis to create a three-dimensional image. In some embodiments, the anatomical image comprises a plurality of three-dimensional images representing a time progression to create a four-dimensional image. In some embodiments, the anatomical image is a histopathology image. In some embodiments, the anatomical image is of a neural sample. In some embodiments, the anatomical image is a confocal micrograph. In some embodiments, the marking comprises making a measurement of the morphological feature or sub-feature. In some embodiments, the score is used for diagnosis of medical conditions or evaluation of pharmacological therapies. In some embodiments, the morphological feature is a feature of a dendrite. In some embodiments, the morphological sub-feature is a feature of a dendritic spine. In some embodiments, the measurement comprises a density, a diameter, a length, or a combination thereof. In some embodiments, the measurement comprises a dendritic spine density, a dendritic spine head diameter, a dendritic spine length, a dendritic spine neck diameter, a dendritic spine distance from a dendrite soma, a dendrite diameter, or a combination thereof. In some embodiments, the application further comprises a database of anatomical images and associated scores.

In another aspect, disclosed herein are non-transitory computer-readable storage media encoded with a computer program including instructions executable by a processor to create a server application comprising: a software module configured to distribute an anatomical image to a plurality of image analyst applications, each image analyst application operated by a human image analyst; a software module configured to receive the anatomical image from the plurality of analyst applications, the received images marked by the image analyst to identify a morphological feature of the image; a software module configured to calculate a score for each image, the score based on the marking; and a software module configured to statistically compare the scores to identify aberrant image analyst practices or image interpretations. In some embodiments, the server application is adapted for rapid throughput image analysis. In some embodiments, the anatomical image is distributed to about 10, about 5, or about 2 image analyst applications. In some embodiments, the anatomical image is a two-dimensional, three-dimensional, or four-dimensional image. In further embodiments, the anatomical image comprises a plurality of two-dimensional images in a Z-axis to create a three-dimensional image. In further embodiments, the anatomical image comprises a plurality of three-dimensional images representing a time progression to create a four-dimensional image. In some embodiments, the anatomical image is a histopathology image. In some embodiments, the anatomical image is of a neural sample. In some embodiments, the anatomical image is a confocal micrograph. In some embodiments, the marking indicates a measurement of the morphological feature. In some embodiments, the score is used for diagnosis of medical conditions or evaluation of pharmacological therapies. In some embodiments, the morphological feature is a feature of a dendrite. In some embodiments, the morphological sub-feature is a feature of a dendritic spine. In some embodiments, the measurement comprises a density, a diameter, a length, or a combination thereof. In some embodiments, the measurement comprises a dendritic spine density, a dendritic spine head diameter, a dendritic spine length, a dendritic spine neck diameter, a dendritic spine distance from a dendrite soma, a dendrite diameter, or a combination thereof. In some embodiments, the application further comprises a database of anatomical images and associated scores.

In another aspect, disclosed herein are computer-implemented systems comprising: a digital processing device comprising an operating system configured to perform executable instructions and a memory device; and a computer program including instructions executable by the digital processing device to create a server application comprising: a software module configured to distribute an anatomical image to a plurality of image analyst applications, each image analyst application operated by a human image analyst; a software module configured to receive the anatomical image from the plurality of analyst applications, the received images marked by the image analyst to identify a morphological feature of the image; a software module configured to calculate a score for each image, the score based on the marking; and a software module configured to statistically compare the scores to identify aberrant image analyst practices or image interpretations. In some embodiments, the server application is adapted for rapid throughput image analysis. In some embodiments, the anatomical image is distributed to about 10, about 5, or about 2 image analyst applications. In some embodiments, the anatomical image is a two-dimensional, three-dimensional, or four-dimensional image. In further embodiments, the anatomical image comprises a plurality of two-dimensional images in a Z-axis to create a three-dimensional image. In further embodiments, the anatomical image comprises a plurality of three-dimensional images representing a time progression to create a four-dimensional image. In some embodiments, the anatomical image is a histopathology image. In some embodiments, the anatomical image is of a neural sample. In some embodiments, the anatomical image is a confocal micrograph. In some embodiments, the marking indicates a measurement of the morphological feature. In some embodiments, the score is used for diagnosis of medical conditions or evaluation of pharmacological therapies. In some embodiments, the morphological feature is a feature of a dendrite. In some embodiments, the morphological sub-feature is a feature of a dendritic spine. In some embodiments, the measurement comprises a density, a diameter, a length, or a combination thereof. In some embodiments, the measurement comprises a dendritic spine density, a dendritic spine head diameter, a dendritic spine length, a dendritic spine neck diameter, a dendritic spine distance from a dendrite soma, a dendrite diameter, or a combination thereof. In some embodiments, the application further comprises a database of anatomical images and associated scores.

In another aspect, disclosed herein are computer-based platforms comprising: a plurality of computers, each computer configured to provide an image analyst application, the application operated by a human image analyst, the application comprising: a software module configured to receive an image from a centralized server; and a software module configured to provide an interface for identifying and marking a feature of the image, the marking comprising making a measurement of the feature; and a server configured to provide a management application comprising: a software module configured to distribute the image to a plurality of the image analyst applications; a software module configured to receive marked images from the analyst applications and calculate a score for each image, the score based on the marking; and a software module configured to statistically compare the scores to identify aberrant image analyst practices or image interpretations. In some embodiments, the image is distributed to about 10, about 5, or about 2 image analyst applications. In some embodiments, the image is a two-dimensional, three-dimensional, or four-dimensional image. In further embodiments, the image comprises a plurality of two-dimensional images in a Z-axis to create a three-dimensional image. In further embodiments, the image comprises a plurality of three-dimensional images representing a time progression to create a four-dimensional image. In some embodiments, the marking comprises making a measurement of the feature. In some embodiments, the measurement comprises a density, a diameter, a length, a distance, an area, or a combination thereof. In some embodiments, the management application further comprises a database of images and associated scores.

BRIEF DESCRIPTION OF THE DRAWINGS

FIG. 5 shows a non-limiting example of an interface for dendrite analysis; in this case, an interface for use by a human image analyst, the interface adapted to allow an image analyst to identify a primary dendrite in an image.

FIG. 6 shows a non-limiting example of an interface for dendrite analysis; in this case, an interface for use by a human image analyst, the interface adapted to allow an image analyst to identify and mark a morphological feature.

DETAILED DESCRIPTION OF THE INVENTION

Figure 1:
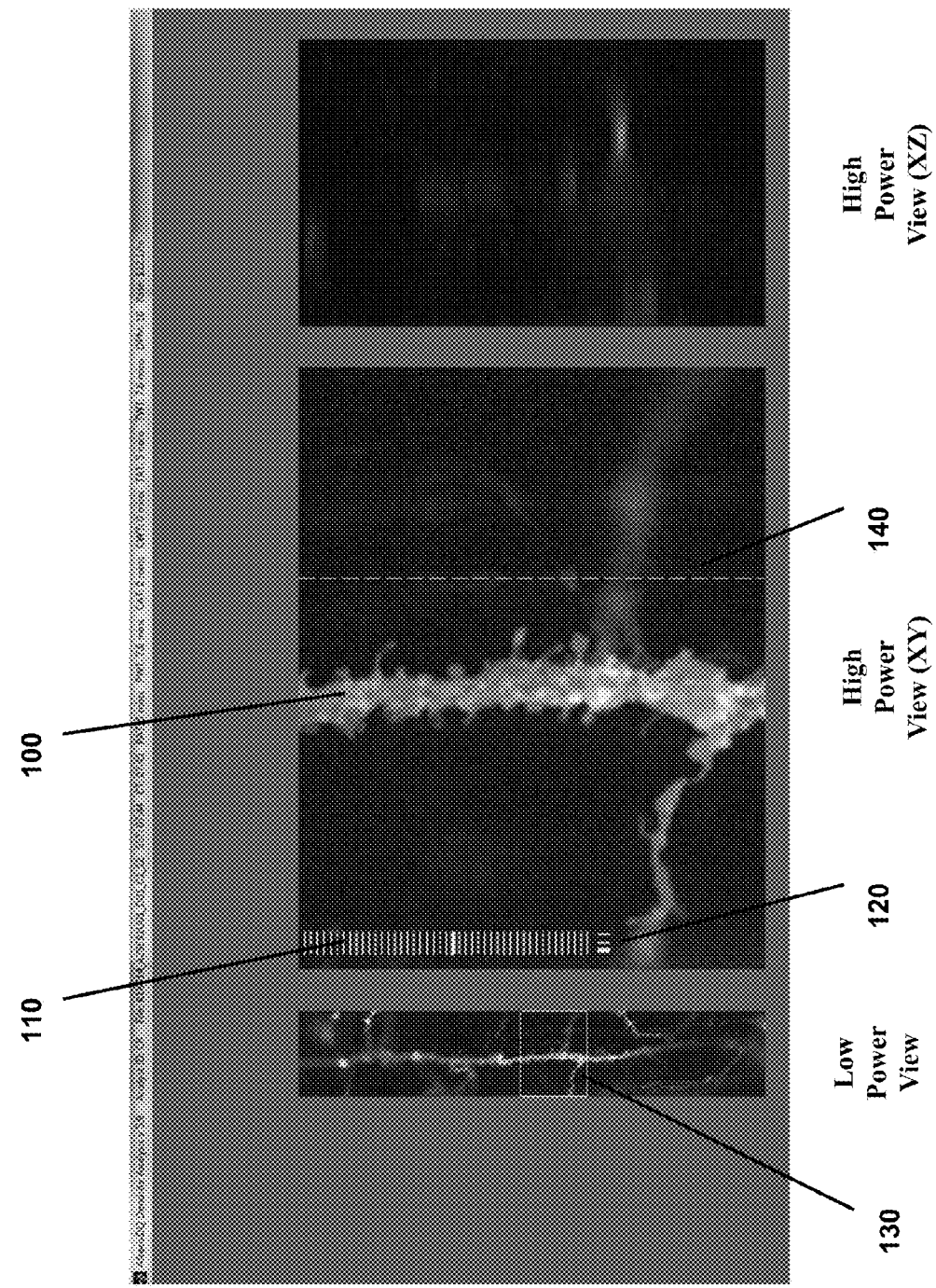
FIG. 1 shows a non-limiting exemplary overview of an interface for dendrite analysis.

Described herein, in certain embodiments, are computer-based platforms comprising: a plurality of computers, each computer configured to provide an image analyst application, the application operated by a human image analyst, the application comprising: a software module configured to receive an anatomical image; and a software module configured to provide an interface for identifying and marking a morphological feature of the image; and a server configured to provide a management application comprising: a software module configured to distribute the anatomical image to a plurality of the image analyst applications; a software module configured to receive marked images from the analyst applications and calculate a score for each image, the score based on the marking; and a software module configured to statistically compare the scores to identify aberrant image analyst practices or image interpretations.

Also described herein, in certain embodiments, are non-transitory computer-readable storage media encoded with a computer program including instructions executable by a processor to create a distributed image analysis application comprising: a software module configured to receive a two-, three-, or four-dimensional anatomical image from a centralized server, the anatomical image provided to a plurality of image analysis applications; a software module configured to provide an interface for viewing the image in three-dimensions, the interface for viewing the image comprising tools for manipulating the image in X and Y axes, and optionally, Z axis, and optionally, time progression; a software module configured to provide an interface for identifying and marking a morphological feature of the image; a software module configured to provide an interface for identifying and marking a morphological sub-feature of the image; and a software module configured to transmit the marked image to the centralized server; provided that the application is adapted for operation by a human image analyst.

Also described herein, in certain embodiments, are computer-implemented systems comprising: a digital processing device comprising an operating system configured to perform executable instructions and a memory device; and a computer program including instructions executable by the digital processing device to create a distributed image analysis application comprising: a software module configured to receive a two-, three-, or four-dimensional anatomical image from a centralized server, the anatomical image provided to a plurality of image analysis applications; a software module configured to provide an interface for viewing the image in three-dimensions, the interface for viewing the image comprising tools for manipulating the image in X and Y axes, and optionally, Z axis, and optionally, time progression; a software module configured to provide an interface for identifying and marking a morphological feature of the image; a software module configured to provide an interface for identifying and marking a morphological sub-feature of the image; and a software module configured to transmit the marked image to the centralized server; provided that the application is adapted for operation by a human image analyst.

Also described herein, in certain embodiments, are non-transitory computer-readable storage media encoded with a computer program including instructions executable by a processor to create a server application comprising: a software module configured to distribute an anatomical image to a plurality of image analyst applications, each image analyst application operated by a human image analyst; a software module configured to receive the anatomical image from the plurality of analyst applications, the received images marked by the image analyst to identify a morphological feature of the image; a software module configured to calculate a score for each image, the score based on the marking; and a software module configured to statistically compare the scores to identify aberrant image analyst practices or image interpretations.

Also described herein, in certain embodiments, are computer-implemented systems comprising: a digital processing device comprising an operating system configured to perform executable instructions and a memory device; and a computer program including instructions executable by the digital processing device to create a server application comprising: a software module configured to distribute an anatomical image to a plurality of image analyst applications, each image analyst application operated by a human image analyst; a software module configured to receive the anatomical image from the plurality of analyst applications, the received images marked by the image analyst to identify a morphological feature of the image; a software module configured to calculate a score for each image, the score based on the marking; and a software module configured to statistically compare the scores to identify aberrant image analyst practices or image interpretations.

Also described herein, in certain embodiments, are computer-based platforms comprising: a plurality of computers, each computer configured to provide an image analyst application, the application operated by a human image analyst, the application comprising: a software module configured to receive an image from a centralized server; and a software module configured to provide an interface for identifying and marking a feature of the image, the marking comprising making a measurement of the feature; and a server configured to provide a management application comprising: a software module configured to distribute the image to a plurality of the image analyst applications; a software module configured to receive marked images from the analyst applications and calculate a score for each image, the score based on the marking; and a software module configured to statistically compare the scores to identify aberrant image analyst practices or image interpretations.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Platform

In some embodiments, described herein is a distributed image analysis platform. In further embodiments, the platform comprises a plurality of image analyst computers, each provided with instructions to create an image analyst application. In further embodiments, the platform comprises one or more servers, each provided with instructions to create a management application. Many hardware/software configurations are suitable. In various embodiments, the platform comprises about 2, 3, 4, 5, 6, 7, 8, 9, 10 or more image analyst applications, each application operated by a human image analyst. In various further embodiments, the platform comprises about 10, 20, 30, 40, 50, 60, 70, 80, 90, 100 or more image analyst applications, including increments therein, each application operated by a human image analyst. In still further various embodiments, the platform comprises about 100, 200, 300, 400, 500, 600, 700, 800, 900, 1000 or more image analyst applications, including increments therein, each application operated by a human image analyst. In still further various embodiments, the platform comprises about 1000, 2000, 3000, 4000, 5000, 6000, 7000, 8000, 9000, 10000 or more image analyst applications, including increments therein, each application operated by a human image analyst. In light of the disclosure provided herein, those of skill in the art will recognize that larger numbers of analysts potentially increases the image processing speed and capacity of the platform. In various embodiments, the platform comprises about 2, 3, 4, 5, 6, 7, 8, 9, 10 or more management applications. In various further embodiments, the platform comprises about 10, 20, 30, 40, 50, 60, 70, 80, 90, 100 or more management applications, including increments therein. In light of the disclosure provided herein, those of skill in the art will recognize that larger numbers of management servers potentially increases the image processing speed and capacity of the platform.

In some embodiments, the image analysis platform is distributed. As used herein, "distributed" refers to a software system in which components are located on distinct networked computers that communicate and coordinate their actions by passing messages in order to achieve a common goal. In some embodiments, the distributed platforms are intranet-based. In some embodiments, the platforms are distributed internet-based. In further embodiments, the distributed platforms are web-based. In some embodiments, the distributed platforms are based on one or more cloud-computing infrastructures or services. In various embodiments, advantages of a distributed platform include, by way of non-limiting examples, high throughput image analysis, redundant or multiply-redundant image analyses, efficient utilization of human resources, and the like.

In some embodiments, the distributed platforms described herein allow utilization of a plurality of distinct human image analysts. In further embodiments, utilization of a plurality of image analysts allows the platforms, systems, media, and methods described herein to receive analysis of each image from more than one analyst. In still further embodiments, the platforms, systems, media, and methods described herein statistically compare a plurality of interpretations, markings, and measurements for each image to identify aberrant or outlier data. In various embodiments, each image is analyzed by about 2, 3, 4, 5, 6, 7, 8, 9, 10, 11, 12, 13, 14, 15, 16, 17, 18, 19, 20 or more image analysts. In particular embodiments, at least 2, at least 3, at least 4, or at least 5 image analysts analyze each image. In some embodiments, interpretations, markings, and measurements from a plurality of image analysts are averaged for each image.

In some embodiments, the distributed analysis described herein offers about a 5, 10, 15, 20, 25, 30, 35, 40, 45, 50, 55, 60, 65, 70, 75, 80, 85, 90, 95, or 100% increase, including increments therein, in accuracy over existing automated software analysis methods. In further embodiments, the high throughput image analysis described herein offers about a 100, 200, 300, 400, 500, 600, 700, 800, 900, or 1000% increase, including increments therein, in accuracy over existing automated software analysis methods.

In some embodiments, the distributed platforms described herein allow, for example, utilization of a plurality of image analysts that are optionally geographically dispersed. In some embodiments, the image analysts are selected without regard to geographic location. For example, in further embodiments, image analysts are selected based on training, expertise, availability, and the like.

In some embodiments, the distributed platforms described herein are completely scalable and allow, for example, high throughput image analysis. In some embodiments, the high throughput image analysis described herein allows, for example, evaluation of about 100000, 200000, 300000, 400000, 500000, 600000, 700000, 800000, 900000, or 1000000 images per month, including increments therein. In further embodiments, the high throughput image analysis described herein allows, for example, evaluation of about 1 million, 2 million, 3 million, 4 million, 5 million, 6 million, 7 million, 8 million, 9 million, or 1 billion images per month, including increments therein.

In some embodiments, the high throughput image analysis described herein offers about a 5, 10, 15, 20, 25, 30, 35, 40, 45, 50, 55, 60, 65, 70, 75, 80, 85, 90, 95, or 100% increase, including increments therein, in throughput over existing human analysis methods. In further embodiments, the high throughput image analysis described herein offers about a 100, 200, 300, 400, 500, 600, 700, 800, 900, or 1000% increase, including increments therein, in throughput over existing human analysis methods. In still further embodiments, the high throughput image analysis described herein offers about a 1000, 2000, 3000, 4000, 5000, 6000, 7000, 8000, 9000, or 10000% increase, including increments therein, in throughput over existing human analysis methods.

Human Image Analyst

In some embodiments, the platforms, systems, media, and methods described herein include a human image analyst. In further embodiments, a human image analyst is able to perceive subtle features of an image despite visual noise, artifacts, and other challenges that hamper automated algorithm-based image analysis tools.

As described herein, in some embodiments, the platforms, systems, media, and methods described herein utilize a plurality of human image analysts, each operating an image analysis application. In some embodiments, the image analysts are located in the in the same place. In other embodiments, the image analysts are located in a variety of locations. For example, in further embodiments, the image analysts are distributed across buildings, campuses, cities, regions, counties, states, countries, or combinations thereof.

In some embodiments, the image analysts possess a particular expertise or training. By way of example, in some embodiments, the images are anatomical images and the image analysts are trained scientists, physicians, nurses, or the like. By way of further example, in some embodiments, the images are surveillance images and the image analysts are trained intelligence analysts, or the like. In a particular embodiment, the image analysts are not selected for a particular expertise or training. In further embodiments, only minimal training is required to analyze the images and operate the image analysis applications described herein.

Anatomical Image

In some embodiments, the platforms, systems, media, and methods described herein include image analysis. In some embodiments, the image depicts any suitable subject matter. A wide range of image subject matter is suitable. Particularly well suited are images wherein interpretation of fine details is important, but the image includes visual noise, artifacts, and the like that complicate entirely automated, software algorithm based methods. In some embodiments, the image is a biological image. In further embodiments, the image is an anatomical image depicting one or more structures of an organism.

In some embodiments, a suitable image is a still image or series of images. Many raster image formats are suitable including, by way of non-limiting examples, Joint Photographic Experts Group (JPEG), JPEG 2000, Exchangeable image file format (Exif), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), wireless bitmap (WBMP), and WebP. In some embodiments, images are uncompressed (e.g., RAW format). In other embodiments, images are compressed. Both lossy and lossless image CODECs are suitable. Many vector image formats are suitable including, by way of non-limiting examples, CGM and SWF.

In some embodiments, a suitable image is a video or series of videos. Many video formats are suitable including, by way of non-limiting examples, Windows® Media Video (WMV), Windows® Media®, Motion Picture Experts Group (MPEG), Audio Video Interleave (AVI), Apple® QuickTime®, RealMedia®, Flash Video, Motion JPEG (M-JPEG), WebM, and Advanced Video Coding High Definition (AVCHD). In some embodiments, video is uncompressed (e.g., RAW format). In other embodiments, video is compressed. Both lossy and lossless video CODECs are suitable including, by way of non-limiting examples, DivX™, Cineform, Cinepak, Dirac, DV, FFV1, H.263, H.264, H.264 lossless, JPEG 2000, MPEG-1, MPEG-2, MPEG-4, On2 Technologies (VP5, VP6, VP7, and VP8), RealVideo, Snow lossless, Sorenson Video, Theora, and Windows Media Video (WMV).

In some embodiments, an image is standard-definition. In other embodiments, an image is high-definition. In further embodiments, a high-definition image includes at least about 1280×about 720 pixels or at least about 1920×about 1080 pixels.

Both two-dimensional and three-dimensional images are suitable. In some embodiments, a suitable three-dimensional image comprises a series of two-dimensional (XY-axes) images spanning a depth (Z-axis). In other embodiments, a suitable three-dimensional image comprises a stereographic image. In yet other embodiments, a suitable three-dimensional image comprises a rendered three-dimensional model.

In some embodiments, a suitable image is a biological image produced by, for example, radiography (e.g., X-ray), ultrasound, tomography (e.g., CT scan, SPECT, etc.), or magnetic resonance imaging (MRI). In some embodiments, a suitable image is a biological diagram produced by, for example, electroencephalography (EEG), magnetoencephalography (MEG), or electrocardiography (EKG).

In some embodiments, a suitable image is a biological image produced by microscopy. Many types of microscopy are suitable including optical (light) microscopy techniques such as, bright field microscopy, dark field microscopy, dispersion staining, phase contrast microscopy, differential interference contrast microscopy, interference reflection microscopy, fluorescence microscopy, light sheet fluorescence microscopy, Super-Resolution microscopy, serial time-encoded amplified microscopy, and confocal microscopy (including optical sectioning). Suitable electron microscopy techniques include transmission electron microscopy (TEM) and scanning electron microscopy (SEM). Suitable scanning probe microscopy techniques include ultrasonic force microscopy (UFM). Other suitable microscopy techniques include, by way of non-limiting examples, ultraviolet microscopy, infrared microscopy, laser microscopy, and digital holographic microscopy.

Image Analyst Application

In some embodiments, the platforms, systems, media, and methods described herein include an image analyst application, or use of the same. In further embodiments, a human image analyst operates the application. The application is suitably provided as an executable standalone application, a web application, a web browser plug-in or extension, a mobile application, or a combination thereof.

Receiving Images

In some embodiments, the platforms, systems, media, and methods described herein include a module configured to receive an image, or use of the same. In further embodiments, the received image is transmitted by a management server application described herein. The image is optionally in a wide range of suitable formats described herein. In particular embodiments, the image is identified by, for example, file name, at the top of the application GUI. In some embodiments, the same image is received by a plurality of image analyst applications to be evaluated by the same number of distinct image analysts. In some embodiments, images are pushed to the image analyst application by a management application running at a centralized server. In further embodiments, images are pushed to the image analyst application at pre-determined time intervals or as the analyst completes evaluation of each image.

In various embodiments, the module configured to receive images utilizes any suitable communications method. In some embodiments, images are transmitted and received utilizing wired or fiber optic telephone communications, wired or fiber optic Internet communications, or the like, including combinations thereof. Images are transmitted and received utilizing a wide variety of suitable wired and wireless communications protocols. In further embodiments, suitable communications protocols include, by way of non-limiting examples, 802.11x (including Wi-Fi), WiMAX, 3G (3rd generation mobile telecommunications), 4G (4th generation mobile telecommunications), LTE (Long Term Evolution), LTE Advanced, and geosynchronous and low Earth orbit (LEO) satellite, or combinations thereof. In further embodiments, suitable communications protocols include, by way of non-limiting examples, transmission control protocol/internet protocol (TCP/IP), hypertext transfer protocol (HTTP), hypertext transfer protocol secure (HTTPS), file transfer protocol (FTP), user datagram protocol (UDP), internet message access protocol (IMAP), post office protocol (POP), simple mail transfer protocol (SMTP), and simple network management protocol (SNMP), or combinations thereof. In some embodiments, received images are encrypted. In further embodiments, images are received securely by utilizing cryptographic protocols such as Secure Sockets Layer (SSL), Transport Layer Security (TLS) for web traffic and/or IPsec for network traffic.

Manipulating Images

In some embodiments, the platforms, systems, media, and methods described herein include an interface for viewing and manipulating images. In further embodiments, the interface includes features for manipulating the image in X- and Y-axes, and optionally, Z-axis, and optionally, time progression, or use of the same. In further embodiments, the interface includes features for manipulating the image by zooming in and out (e.g., manipulating scale, magnification, etc.). In some embodiments, the interface further includes features for adjusting the gamma of the images.

In some embodiments, an image analyst interacts with the interface to manipulate images via one or more input devices. In some embodiments, the input device is a keyboard. In further embodiments, the image analyst manipulates images with keystrokes, keystroke combinations, or the like. In some embodiments, the input device is a pointing device including, by way of non-limiting examples, a mouse, trackball, track pad, joystick, game controller, or stylus. In further embodiments, the image analyst manipulates images with clicks, double clicks, drawing, drags, hovers, or the like. In some embodiments, the input device is a touch screen or a multi-touch screen. In further embodiments, the image analyst manipulates images with taps (one or more fingers), double taps, swipes (one or more fingers), pinches, reverse pinches, or the like. In other embodiments, the input device is a microphone to capture voice or other sound input. In other embodiments, the input device is a video camera or other sensor to capture motion or visual input. In further embodiments, the input device is a Kinect, Leap Motion, or the like.

Referring to FIG. 1, in a particular embodiment, an interface for dendrite analysis displays a three-dimensional neurological image. Specifically, an image of a dendrite 100 produced by confocal microscopy. The interface includes three main viewing windows: a low power view to provide a visual overview of the image, a high power view in the XY plane, and a high power view in the XZ plane (analogous to viewing the high power XY view on its side). In this embodiment, the interface includes a z-slider indicator 110 to indicate the displayed depth of the image and a resize indicator 120 to indicate the displayed scale of the image. The low power viewing window includes an XY bounding box 130 to indicate the current area displayed in the high power viewing windows. The high power viewing window for the XY plane includes a XZ position indicator 140 to indicate the current plane displayed in the high power viewing window for the XZ plane. In this embodiment, across the top of the interface the name of the currently displayed image and online analysis tracking data are displayed.

Figure 2:
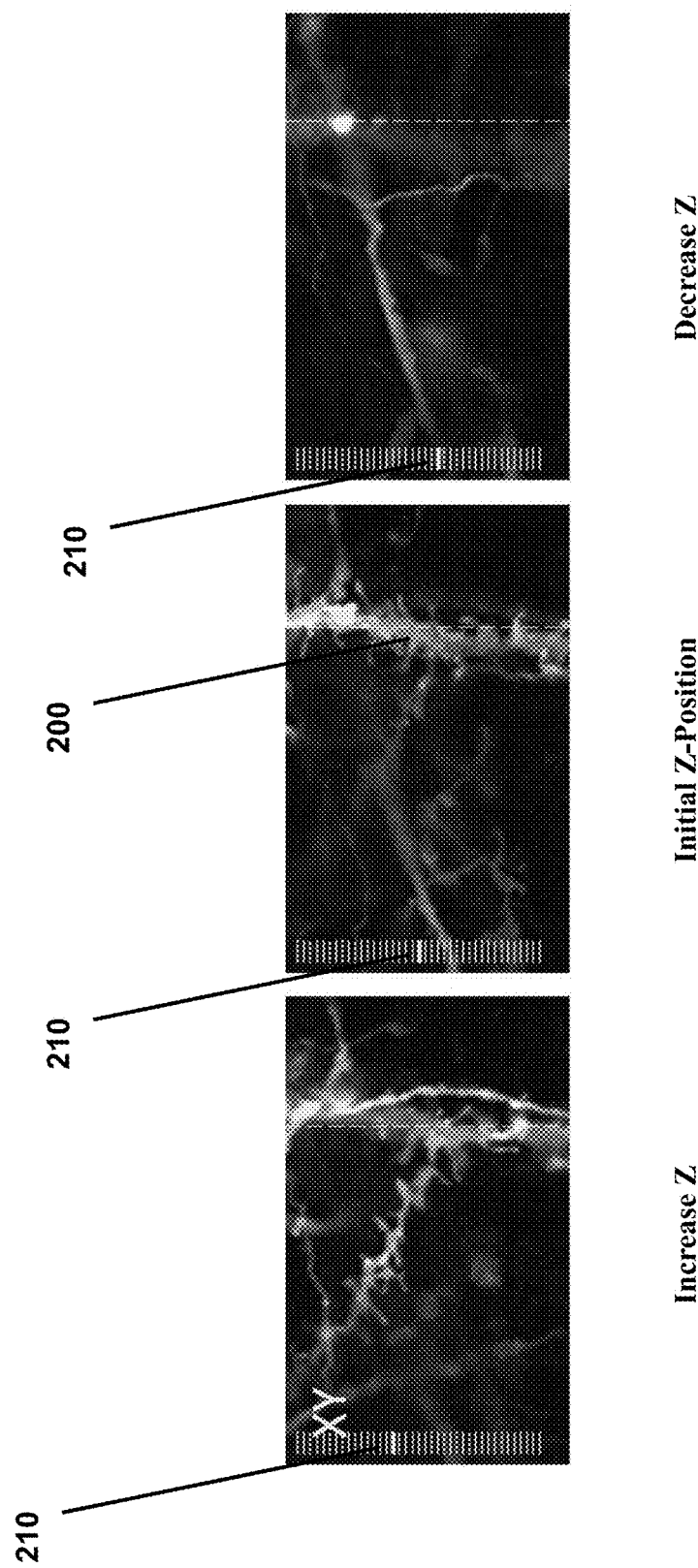
FIG. 2 shows a non-limiting example of an interface for dendrite analysis; in this case, an interface for use by a human image analyst, the interface adapted to allow an image analyst to traverse the Z-axis in a three dimensional image.

Referring to FIG. 2, in a particular embodiment, the displayed image is composed of multiple adjacent images (Z-planes) that create a three-dimensional composition of a neurological sample 200. In this embodiment, the interface includes features to increase and decrease the currently displayed Z-position. When the image analyst adjusts the Z-position, a Z-slider 210 changes accordingly to indicate the currently displayed Z-plane.

Figure 3:
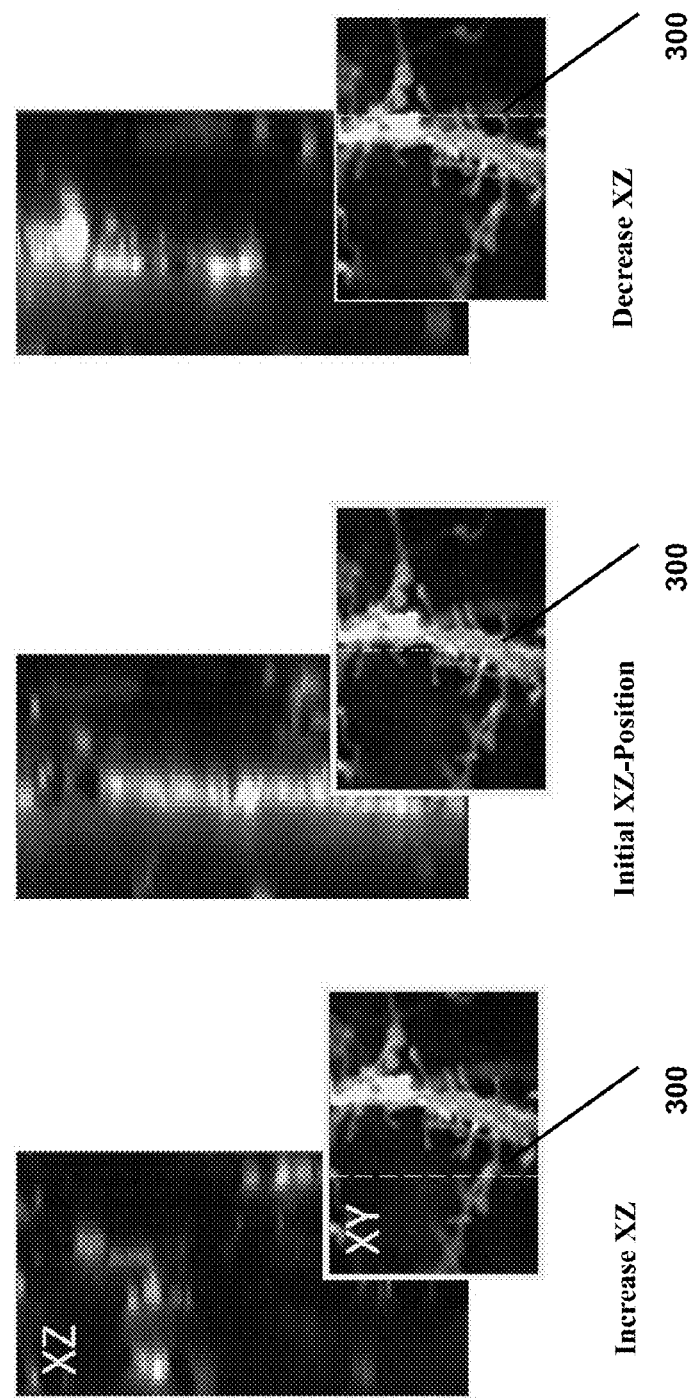
FIG. 3 shows a non-limiting example of an interface for dendrite analysis; in this case, an interface for use by a human image analyst, the interface adapted to allow an image analyst to traverse the X-plane in a three dimensional image.

Referring to FIG. 3, in a particular embodiment, the interface for dendrite analysis includes features to increase and decrease the currently displayed XZ-position. The image analyst adjusts the XZ-position to find the best Z-plane for identifying features of the image. In this embodiment, the high power viewing window for the XY plane includes a XZ position indicator 300 to indicate the current plane displayed in the high power viewing window for the XZ plane.

Figure 4:
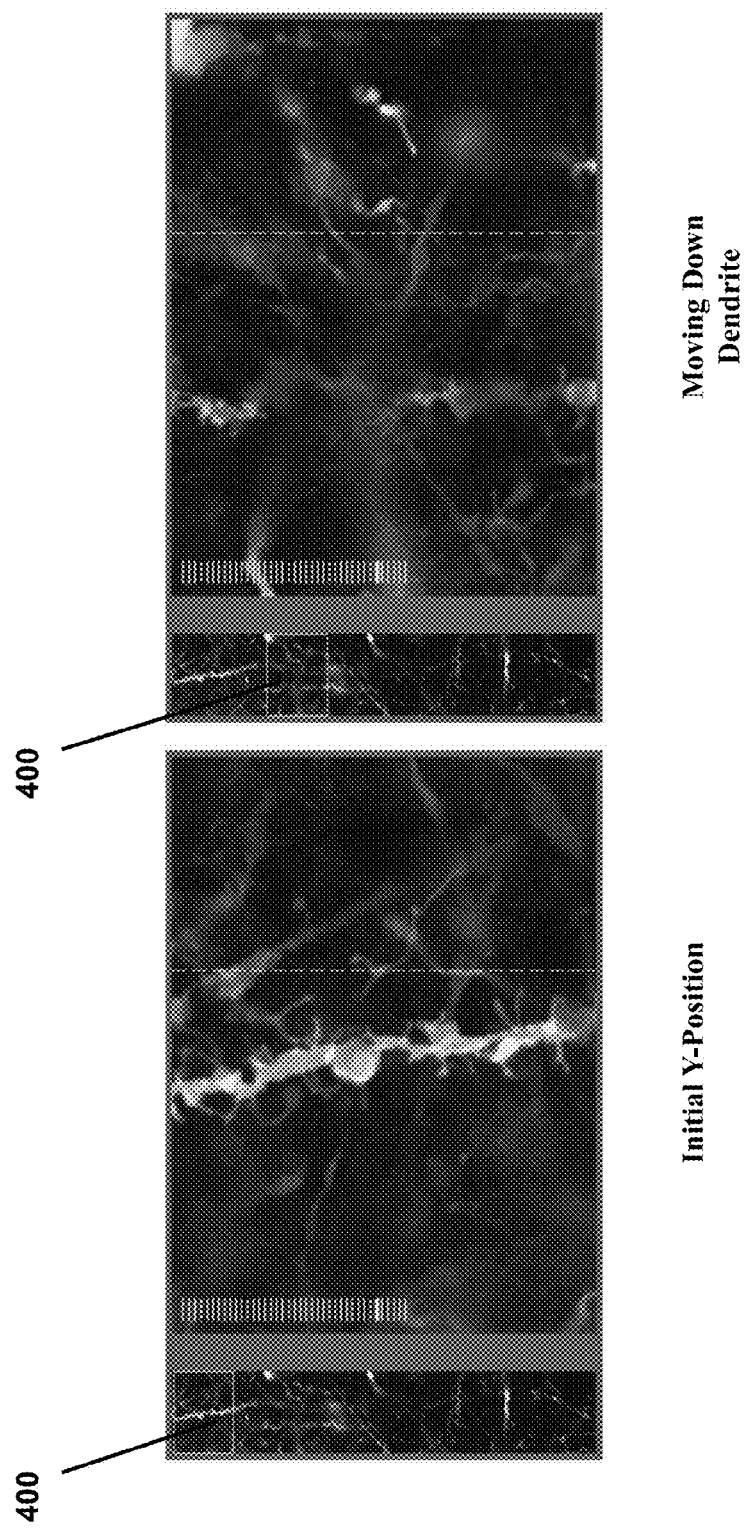
FIG. 4 shows a non-limiting example of an interface for dendrite analysis; in this case, an interface for use by a human image analyst, the interface adapted to allow an image analyst to traverse the Y-axis to follow a feature in an image.

Referring to FIG. 4, in a particular embodiment, the interface for dendrite analysis includes features to increase and decrease the currently displayed Y-position. The low power view displays an entire dendrite in a confocal micrograph. The high power XY view displays a zoomed-in portion of the dendrite and an XY bounding box 400 indicates which portion of the dendrite is shown in the high power view. When the image analyst adjusts the Y-position, the XY bounding box 400 changes accordingly to indicate the currently displayed Y-position on the low power view.

Referring to FIG. 5, in a particular embodiment, a three-dimensional neurological image includes a single dendrite that is intended for analysis (called the primary dendrite), which extends from the top of the image to the bottom of the image. In this embodiment, an image analyst scrolls through the Z-planes while examining the low power view to identify and view the length of the primary dendrite.

Figure 10:
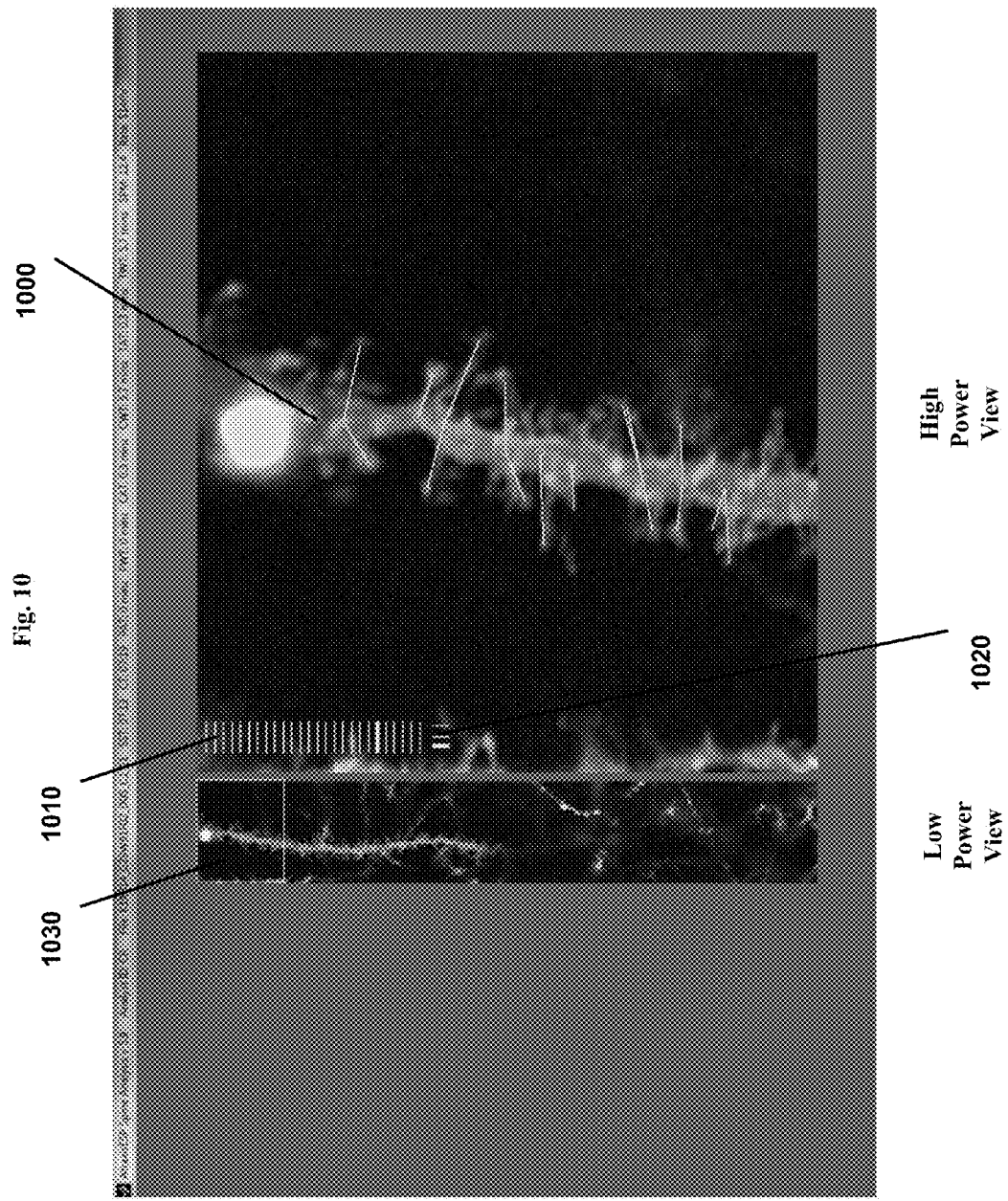
FIG. 10 shows a non-limiting exemplary overview of an interface for dendritic spine quantification.

Referring to FIG. 10, in a particular embodiment, an interface for dendritic spine quantification displays a three-dimensional neurological image. Specifically, a confocal micrograph of a dendrite backbone 1000 with a plurality of dendritic spines. The interface includes two main viewing windows: a low power view to provide a visual overview of the image and a high power view to display a zoomed-in portion of the image. In this embodiment, the interface includes a z-slider indicator 1010 to indicate the displayed depth of the image and a measurement interval indicator 1020 to indicate the displayed scale of the image. The low power viewing window includes an XY bounding box 1030 to indicate the current area displayed in the high power viewing window. The high power viewing window. In this embodiment, across the top of the interface the name of the currently displayed image and online analysis tracking data are displayed.

Figure 11:
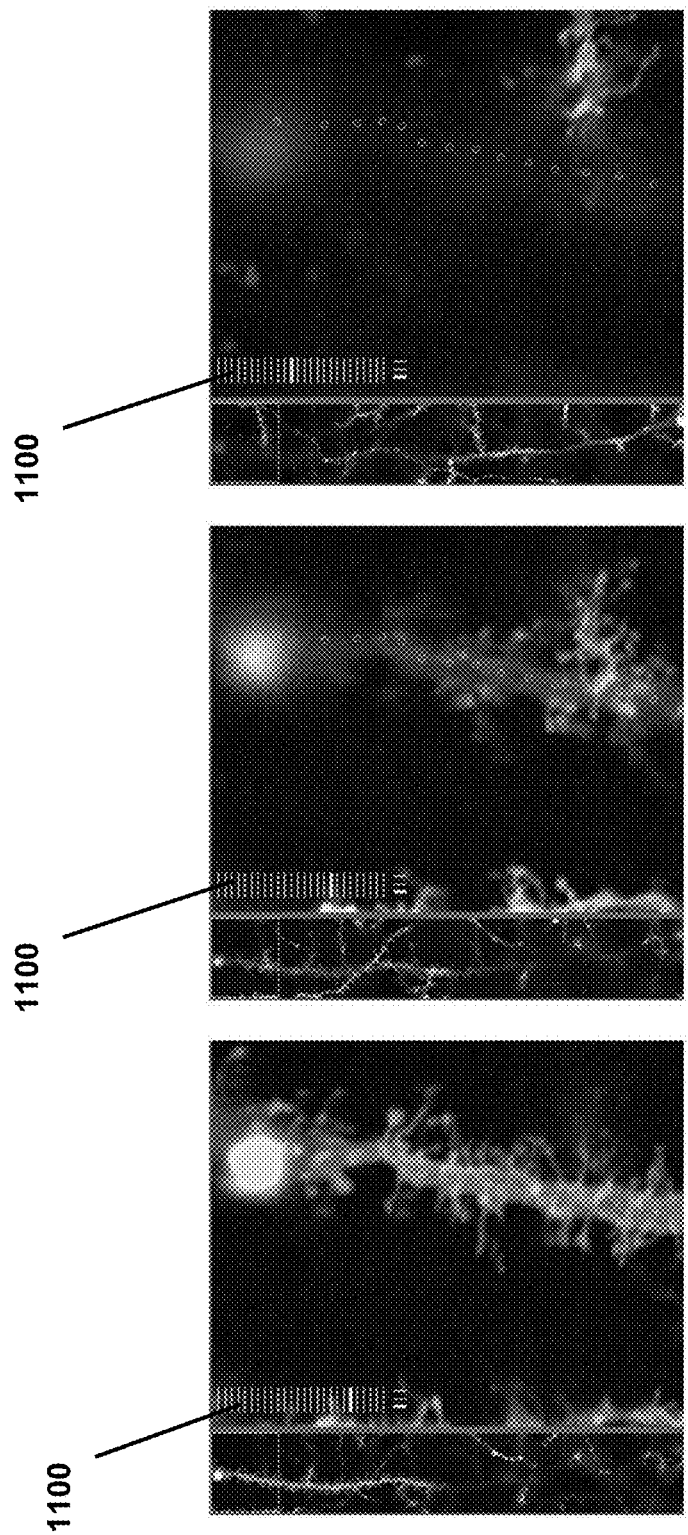
FIG. 11 shows a non-limiting example of an interface for dendritic spine quantification; in this case, an interface for use by a human image analyst, the interface adapted to allow an image analyst to traverse the Z-axis in a three dimensional image.

Referring to FIG. 11, in a particular embodiment, the displayed image is composed of multiple adjacent images (Z-planes) that create a three-dimensional composition of a neurological sample (e.g., a dendrite backbone with a plurality of dendritic spines). In this embodiment, the interface includes features to increase and decrease the currently displayed Z-position. When the image analyst adjusts the Z-position, a Z-slider 1100 changes accordingly to indicate the currently displayed Z-plane.

Figure 12:
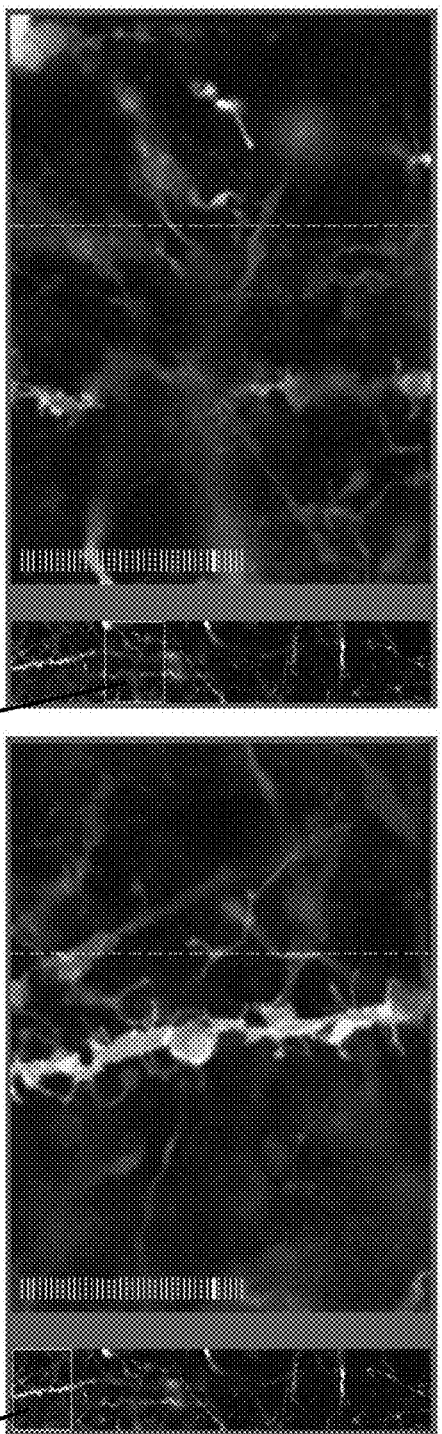
FIG. 12 shows a non-limiting example of an interface for dendritic spine quantification; in this case, an interface for use by a human image analyst, the interface adapted to allow an image analyst to traverse the Y-axis to follow a feature in an image.

Referring to FIG. 12, in a particular embodiment, the interface for dendritic spine quantification includes features to increase and decrease the currently displayed Y-position. The low power view displays an entire dendrite with a plurality of dendritic spines in a confocal micrograph. The high power XY view displays a zoomed-in portion of the dendrite and an XY bounding box 1200 indicates which portion of the dendrite is shown in the high power view. When the image analyst adjusts the Y-position, the XY bounding box 1200 changes accordingly to indicate the currently displayed Y-position on the low power view.

Morphological Features

In some embodiments, the platforms, systems, media, and methods described herein include an interface for identifying features (or sub-features) of an image, or use of the same. In further embodiments, the image is an anatomical image and the interface is for identifying morphological features (or sub-features) of the image. In further embodiments, interface for identifying features allows the image analyst to mark the features. In still further embodiments, interface for identifying features allows the image analyst to measure the features.

For example, in neurological samples, dendritic spine morphology underlies synaptic plasticity and correlates with synaptic strength. Moreover, dendritic spine abnormalities underlie many CNS disorders such as autism spectrum disorder, schizophrenia, and Alzheimer's disease, and spine deficits in disease models mimic human anatomy. As such, dendritic spine measurement and classification (e.g., phenotyping) is useful for CNS drug discovery including unwanted effect and efficacy evaluation. The diverse morphology of dendritic spines; however, presents a challenge to quantification.

Figure 13:
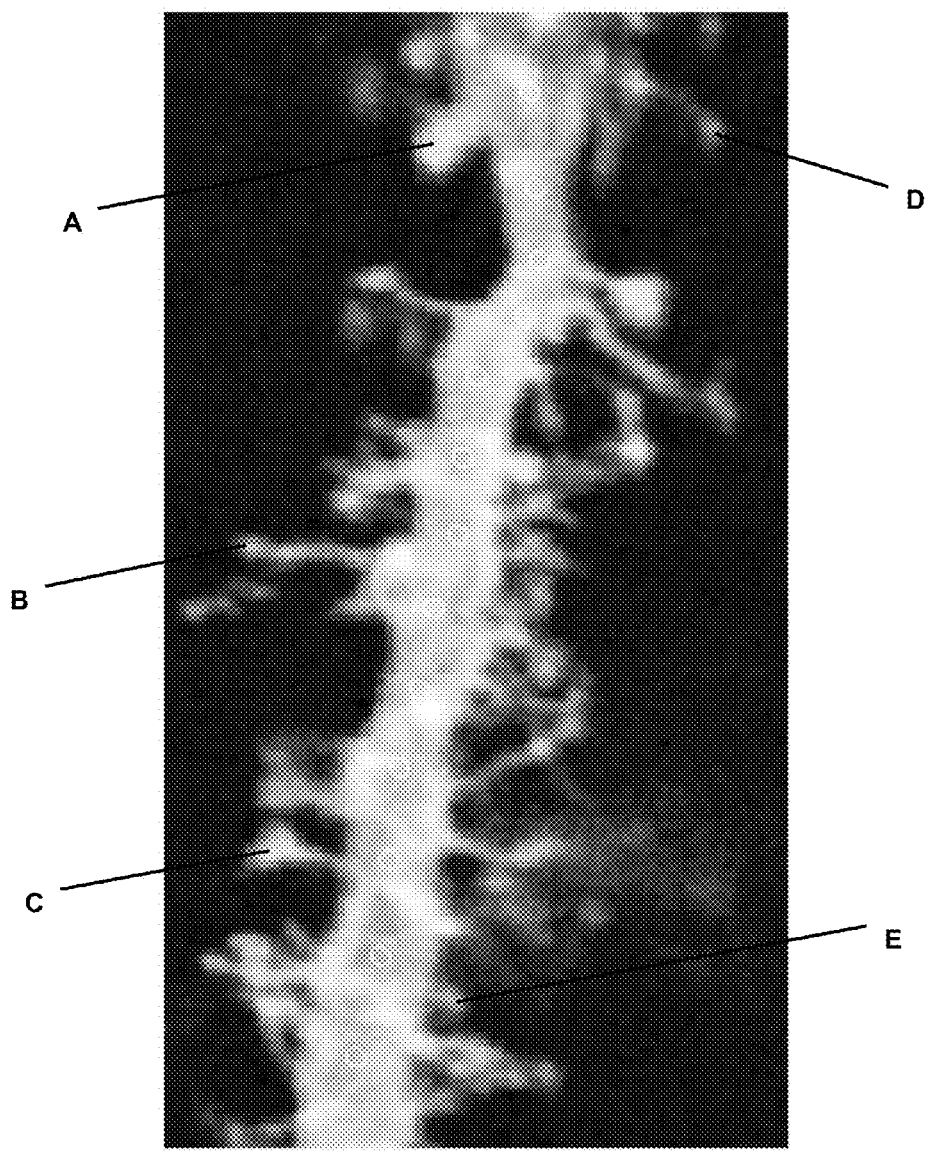
FIG. 13 shows a non-limiting example of a micrograph of a dendrite depicting a wide variety of dendritic spine morphologies.

Referring to FIG. 13, for example, dendritic spines come in a variety of shapes and sizes. Examples include (A) large head and thick neck, (B) small head and long, thin neck, (C) large head and thin neck, (D) medium head and long neck, and (E) small head and short neck.

In some embodiments, the platforms, systems, media, and methods described herein include an interface offering features for identification and measurement of dendritic spine morphological features. In further embodiments, the interface allows image analysts to measure, by way of non-limiting examples, spine density, spine head diameter, spine length, neck diameter, distance from soma of the dendrite, dendrite diameter, and the like. In some embodiments, the dendritic spine measurements are used to score and subsequently classify neurological samples. For example, phenotype spines, based on the morphological measurements on a scale from immature, to intermediate, to mature. In further embodiments, a plurality of scores for a particular image are statistically compared across distinct image analysts. In such embodiments, the platforms, systems, media, and methods described herein include an interface offer an unbiased measurement-based approach to image classification.

In some embodiments, an image analyst interacts with the interface to mark and measure features of images via one or more input devices. In some embodiments, the input device is a keyboard. In further embodiments, the image analyst marks and measures features of images with keystrokes, keystroke combinations, or the like. In some embodiments, the input device is a pointing device including, by way of non-limiting examples, a mouse, trackball, track pad, joystick, game controller, or stylus. In further embodiments, the image analyst marks and measures features of images with clicks, double clicks, drawing, drags, hovers, or the like. In some embodiments, the input device is a touch screen or a multi-touch screen. In further embodiments, the image analyst marks and measures features of images with taps (one or more fingers), double taps, swipes (one or more fingers), pinches, reverse pinches, or the like. In other embodiments, the input device is a microphone to capture voice or other sound input. In other embodiments, the input device is a video camera or other sensor to capture motion or visual input. In further embodiments, the input device is a Kinect, Leap Motion, or the like.

Referring to FIG. 6, in a particular embodiment, an interface for dendrite analysis displays a three-dimensional neurological image. Specifically, an image of a dendrite produced by confocal microscopy. In this embodiment, the interface includes features allowing an image analyst to identify and mark dendrite nodes. In this embodiment, an image analyst uses a mouse to mark a dendrite node on the image with a circular indicator 600. In further embodiments, the image analyst positions the circular marking to identify the position of the dendrite node in three dimensions. New nodes are optionally added in either high power XY or XZ views.

Figure 7:
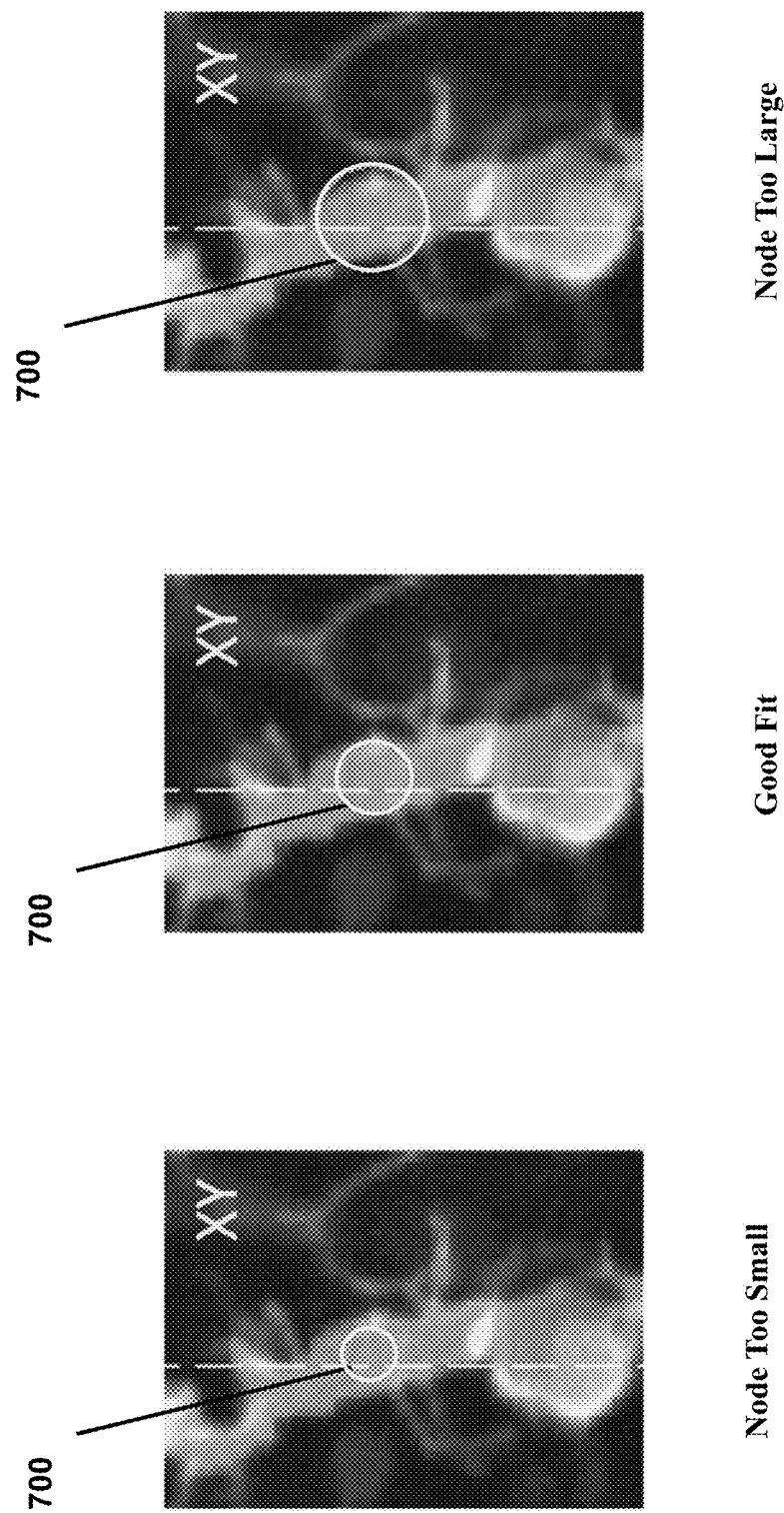
FIG. 7 shows a non-limiting example of an interface for dendrite analysis; in this case, an interface for use by a human image analyst, the interface adapted to allow an image analyst to adjust a marking to indicate the size of a morphological feature.

Referring to FIG. 7, in a particular embodiment, an interface for dendrite analysis includes features allowing an image analyst to identify the size of dendrite nodes. In this embodiment, an image analyst uses a mouse scroll wheel to adjust the size of a circular marking 700 to identify the size of a marked dendrite node. In this embodiment, the image analyst's goal is to set the node diameter to match the width of the dendrite in the XY view at the location of the node.

Figure 8:
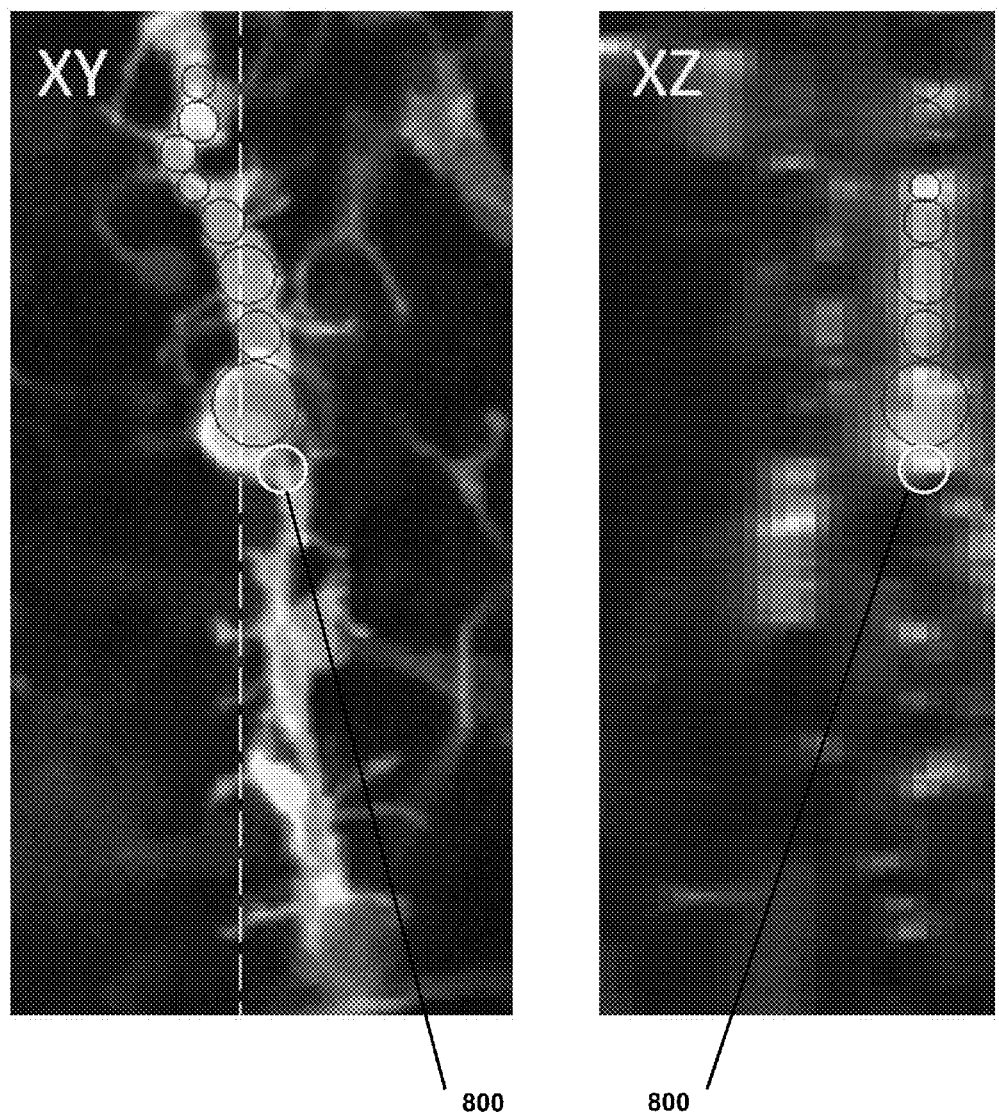
FIG. 8 shows a non-limiting example of an interface for dendrite analysis; in this case, an interface for use by a human image analyst, the interface adapted to allow an image analyst to mark a series of morphological features.

Referring to FIG. 8, in a particular embodiment, an image analyst uses an interface for dendrite analysis to continue to add new nodes to the image of the dendrite. In this embodiment, the analyst adjusts the Y-position of the image as necessary to add nodes to the entire length of the primary dendrite. Further in this embodiment, the optimal position for each node is just adjacent to the previous node on the dendrite and dendrite nodes should cover the entire dendrite.

Figure 9:
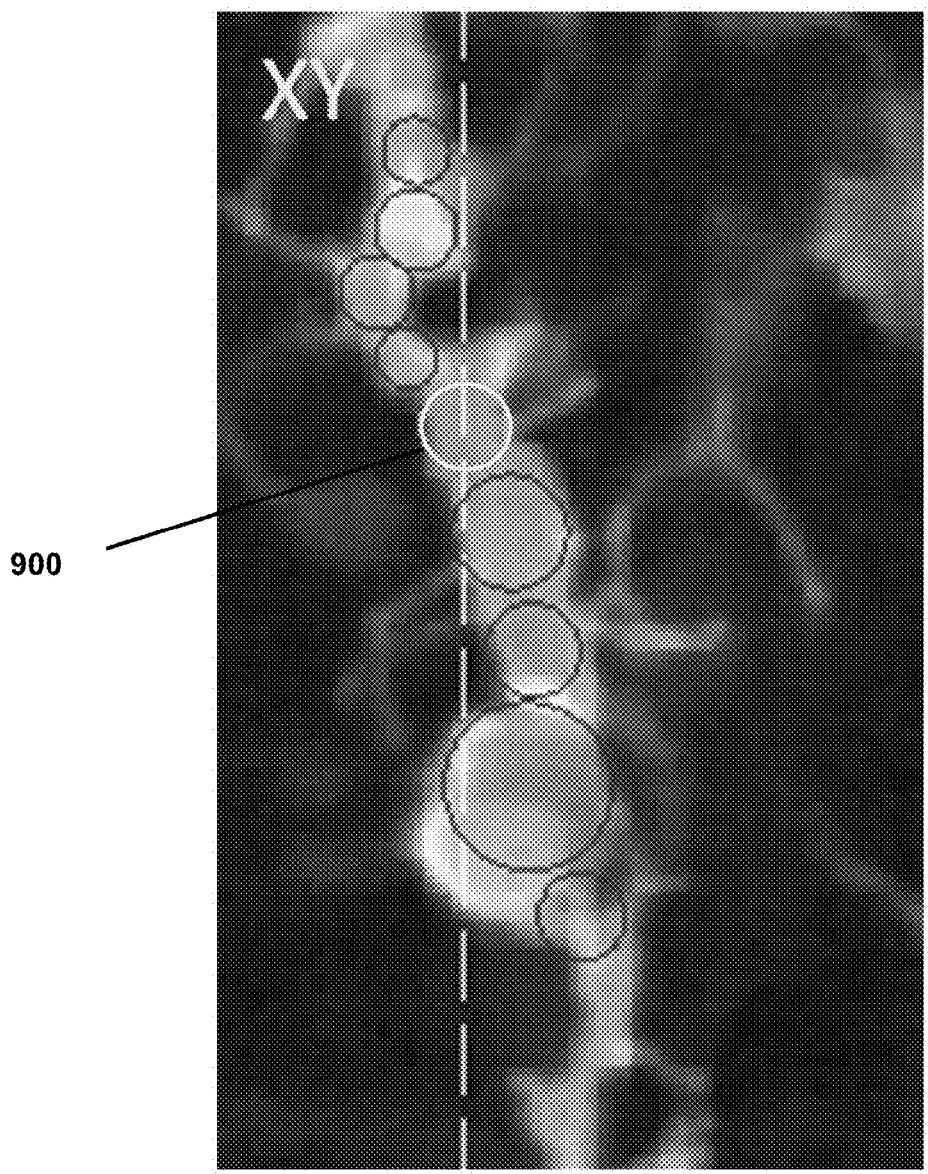
FIG. 9 shows a non-limiting example of an interface for dendrite analysis; in this case, an interface for use by a human image analyst, the interface adapted to allow an image analyst to edit markings that indicate morphological features.

Referring to FIG. 9, in a particular embodiment, an interface for dendrite analysis includes features for editing nodes after it is added. In this embodiment, the analyst clicks a node to highlight it and optionally adjusts its position or size. In further embodiments, the highlighted node is optionally deleted.

Figure 14:
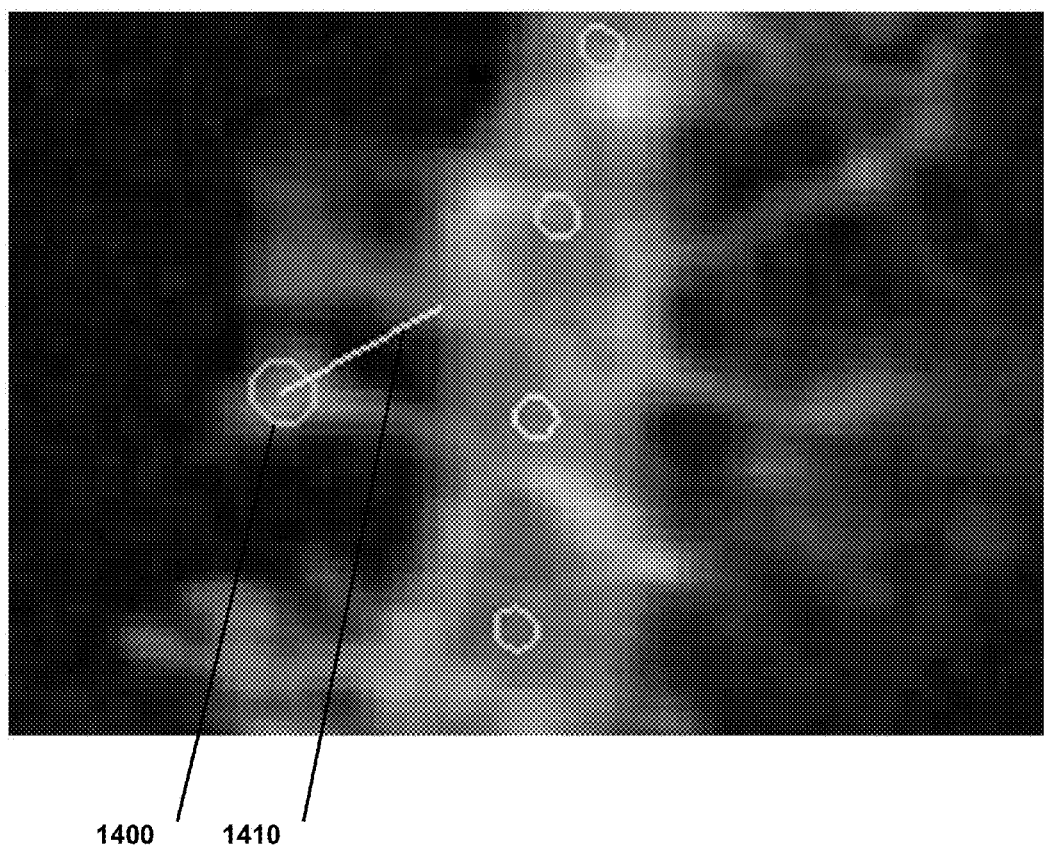
FIG. 14 shows a non-limiting example of an interface for dendritic spine quantification; in this case, an interface for use by a human image analyst, the interface adapted to allow an image analyst to identify and mark a morphological feature.

Referring to FIG. 14, in a particular embodiment, an interface for dendritic spine quantification displays a three-dimensional neurological image. Specifically, an image of a dendrite with multiple dendritic spines produced by confocal microscopy. In this embodiment, the interface includes features allowing an image analyst to identify and mark dendritic spines. In this embodiment, an image analyst uses a mouse to mark a dendritic spine head on the image with a circular indicator 1400. In further embodiments, the image analyst positions the circular marking to identify the position of the dendritic spine head in three dimensions. Also in this embodiment, a linear indicator 1410 marks the spine's neck length. The image analyst uses their mouse to position the linear indicator, connecting it to the best dendrite node attachment point.

Figure 15:
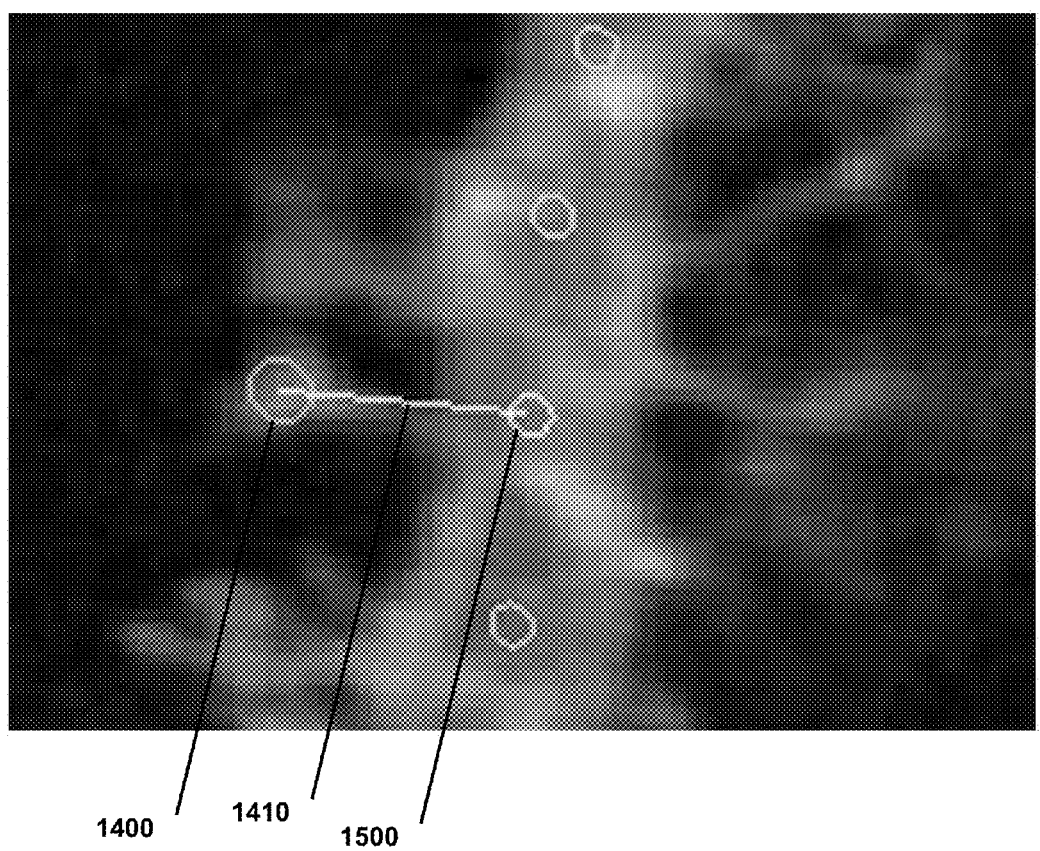
FIG. 15 shows a non-limiting example of an interface for dendritic spine quantification; in this case, an interface for use by a human image analyst, the interface adapted to allow an image analyst to associate morphological features in an image.
Figure 16:
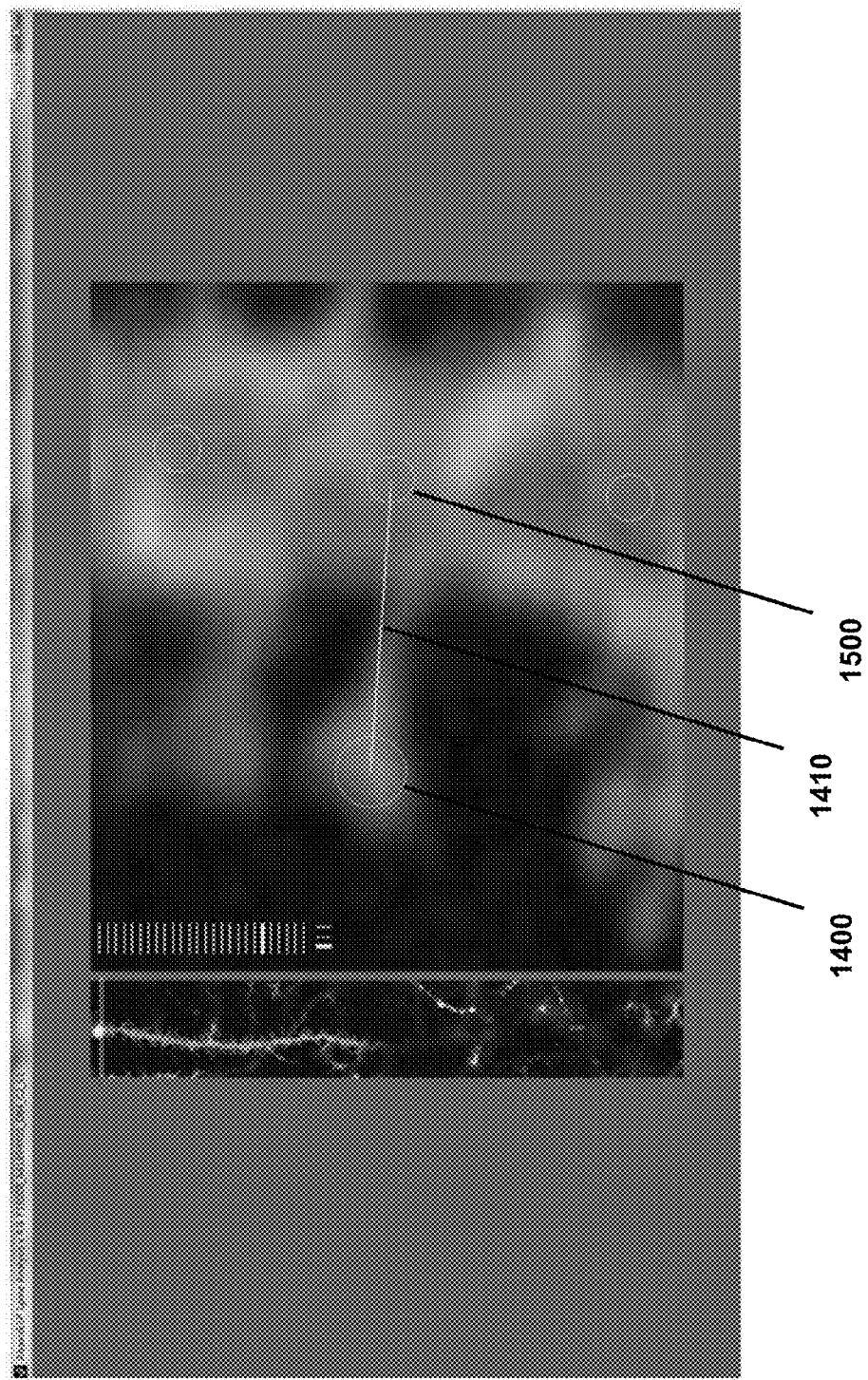
FIG. 16 shows a non-limiting example of an interface for dendritic spine quantification; in this case, an interface for use by a human image analyst, the interface adapted to allow an image analyst to measure the diameter of a morphological feature.

Referring to FIG. 15, in a particular embodiment, an image analyst uses an interface for dendritic spine quantification to mark a dendritic spine head and measure its diameter. In this embodiment, the image analyst connects the spine head to the nearest dendrite node 1500 to mark the spine neck and measure its length. See also, FIG. 16

Figure 17:
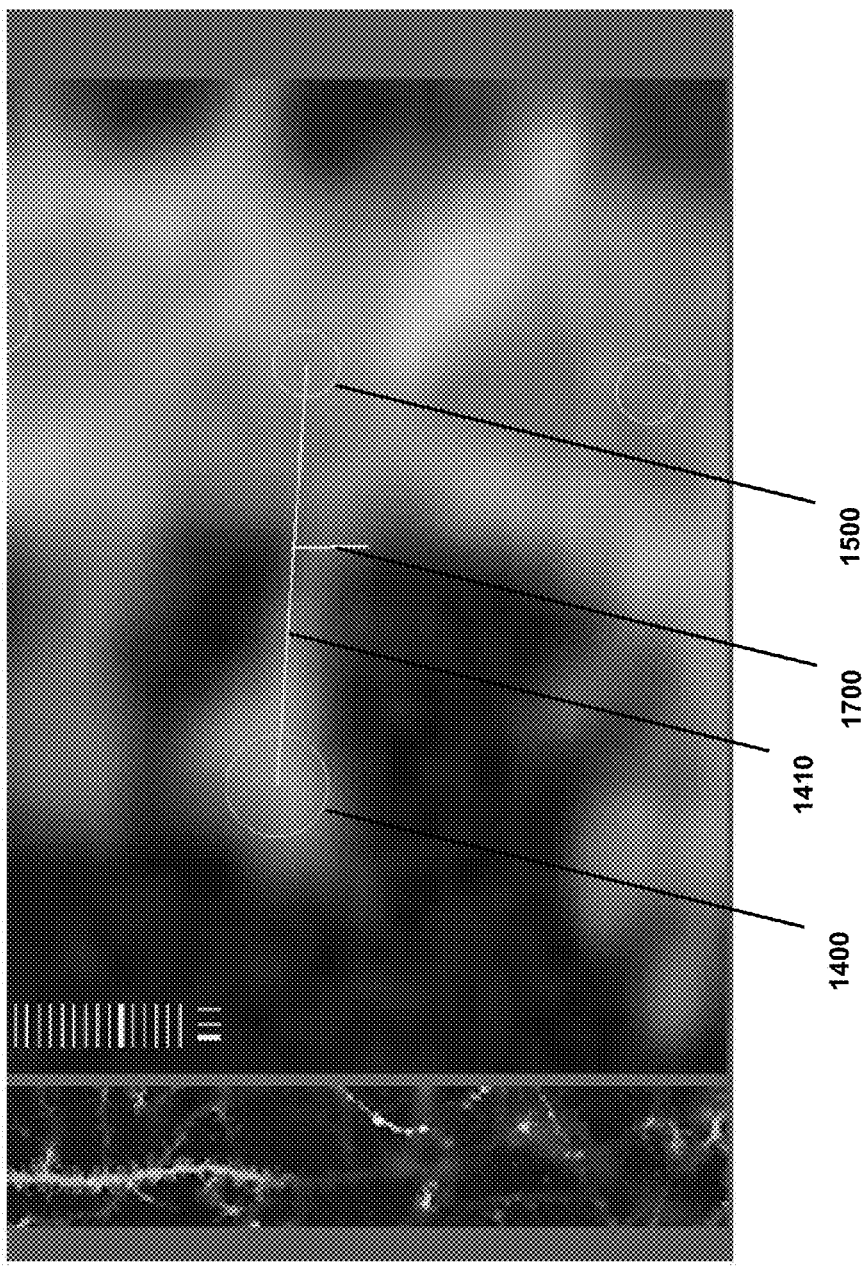
FIG. 17 shows a non-limiting example of an interface for dendritic spine quantification; in this case, an interface for use by a human image analyst, the interface adapted to allow an image analyst to measure the length of a morphological feature.

Referring to FIG. 17, in a particular embodiment, an interface for dendritic spine quantification includes features for measuring the diameter of a dendritic spine neck. In this embodiment, an image analyst has marked the spine head 1400 and connected the length measurement indicator 1410 to a dendrite node 1500. In this embodiment, an image analyst clicks with a mouse on one side of the spine neck to begin the measurement. A line appears and follows the image analyst's cursor to indicate the measurement 1700. Further in this embodiment, the analyst clicks again to set the neck diameter measurement.

In some embodiments, the analyst identifies, marks, and measures, all of the dendritic spines on the primary dendrite. In some embodiments, when the analysis of an image is complete the image analyst activates a feature of the image analysis application that transmits the analysis to a central management application described herein.

The analytical actions performed by the image analyst are tracked and recorded in a local log file or by a management application described herein. In further embodiments, tracked actions include, by way of non-limiting examples, current session start time, current time, previous analysis time, previous wait time, current analysis time, current wait time, total analysis time, total wait time, spines per minute, and analysis billing rate.

In one embodiment, a suitable image analysis workflow comprises:

1. Adjust Z-position to find spine head.
2. Left mouse click on spine to select spine head.
3. Left mouse click on dendrite backbone.
4. View will switch to a zoom mode automatically.
5. Adjust spine head position using left mouse click and drag spine head selection (or use optional equivalent key commands).
6. Adjust spine head size using mouse roller ball (or use optional equivalent key commands).
7. Neck line tool will be ready automatically once you move the mouse off the spine head.
8. Left mouse click to select upper boundary of spine neck.
9. Mouse drag yellow spine neck selection to lower boundary of spine neck.
10. View will automatically revert to normal mode.
11. Repeat steps 1-9 until all spines within view are completed.
12. Move Y-axis to lower position to complete entire dendrite.
13. Transmit (e.g., upload, etc.) completed analysis.

Management Application

In some embodiments, the platforms, systems, media, and methods described herein include a management application, or use of the same. In further embodiments, a management application runs on a centralized server, cluster of servers, or a cloud-based system. In still further embodiments, the management application described herein communicates with each of a plurality of remote image analyst applications. In various embodiments, the management application, for example, coordinates distribution of images for analysis, receives analysis for distributed images, calculates scores for characterization of the images, and performs statistical comparisons for quality control.

Distributing Images

In some embodiments, the platforms, systems, media, and methods described herein include a module configured to distribute an image, or use of the same. In some embodiments, the module configured to distribute an image distributes the image to a plurality of image analyst applications operated by image analysts. In further embodiments, the image is distributed to each of the image analyst applications simultaneously or substantially simultaneously. In other embodiments, the image is distributed to each of the image analyst applications different times. In some embodiments, the image is an anatomical image and is distributed to a plurality of image analysts for morphological (e.g., phenotypic, etc.) analysis.

In various embodiments, the module configured to distribute images utilizes any suitable communications method. In some embodiments, images are distributed utilizing wired or fiber optic telephone communications, wired or fiber optic Internet communications, or the like, including combinations thereof. Images are distributed utilizing a wide variety of suitable wired and wireless communications protocols. In further embodiments, suitable communications protocols include, by way of non-limiting examples, 802.11x (including Wi-Fi), WiMAX, 3G (3rd generation mobile telecommunications), 4G (4th generation mobile telecommunications), LTE (Long Term Evolution), LTE Advanced, and geosynchronous and low Earth orbit (LEO) satellite, or combinations thereof. In further embodiments, suitable communications protocols include, by way of non-limiting examples, transmission control protocol/internet protocol (TCP/IP), hypertext transfer protocol (HTTP), hypertext transfer protocol secure (HTTPS), file transfer protocol (FTP), user datagram protocol (UDP), internet message access protocol (IMAP), post office protocol (POP), simple mail transfer protocol (SMTP), and simple network management protocol (SNMP), or combinations thereof. In some embodiments, received images are encrypted. In further embodiments, images are distributed securely by utilizing cryptographic protocols such as Secure Sockets Layer (SSL), Transport Layer Security (TLS) for web traffic and/or IPsec for network traffic.

Scoring

In some embodiments, the platforms, systems, media, and methods described herein include a module configured to calculate a score for each image, or use of the same. In further embodiments, the score is calculated based on the marking. In still further embodiments, the score is calculated based on the number of markings and the size of each marking indicating a measurement of an image feature. In various embodiments, a score or series of scores represents a measurement of the morphology of dendritic spines in a neuroanatomic image. In further embodiments, a score represents a measurement of, for example, spine density, spine head diameter, spine, length, neck diameter, distance of head from soma of dendrite, dendrite diameter, or a combination thereof.

In some embodiments, the score is a numeric score such as an integer, fraction, or decimal. In other embodiments, the score is a percentage score. In yet embodiments, the score is a letter grade. In some embodiments, a score represents a position on a pre-determined scale. In further embodiments, a score represents a position on a pre-determined dendritic spine morphology scale. In some embodiments, a score represents a class, in a pre-determined catalog of classes. In further embodiments, a score represents a class, in a pre-determined catalog of dendritic spine morphology classes. In a particular embodiment, 3D data partitioning is utilized to organize scores. In further embodiments, a 3D data partitioning scheme comprises spine length on the x-axis, spine neck diameter on the y-axis, and spine head diameter on the z-axis.

Statistical Comparison

In some embodiments, the platforms, systems, media, and methods described herein include a module configured to statistically compare scores, or use of the same. In further embodiments, statistical comparison of scores is performed across analysts for each image in order to identify aberrant image analyst practices or image interpretations.

By way of example, in some embodiments, outlier assessment is performed per image analyst. In such embodiments, each image file is analyzed fully independently by more than one analyst. Each image file contains n number of elements (spines) to be analyzed for m number of measures each (e.g., head diameter, length, etc). Each spine also contains attributes that are recorded (e.g., x, y, z coordinate location). In an exemplary embodiment, analysts are determined to be outliers by the following process:

1) Multiple analyses of the same image must pass criteria: e.g., >90% of elements contain equivalent attributes.

2) If two analysts are used and criteria are not met, then a third analyst is used. The analyst for which criteria are met in relation to the third analyst is retained and the analysis for the analyst for which criteria was not met for either of the other two analysts is eliminated from analysis for that image.

3) If three analysts are used per image by default, then all analysts meeting criteria with at least one other analyst are retained for that image. Any analysts which do not meet criteria with at least one other analyst are eliminated from analysis for that image.

4) For schemes involving >3 analysts per image, a secondary criteria is established for the percentage of analysts that any given analyst must meet the primary criteria with to be retained for analysis for that image.

By way of further example, in some embodiments, outlier assessment is performed per study analyst. In such embodiments, each study contains i number of images that are analyzed and meet criteria according the rules above. In an exemplary embodiment, the following rules are applied to determine whether or not sufficient confidence is established for an individual analyst to be retained for the study. In cases where criteria is not met, all images for which the analyst contributed are removed from final analysis and possibly returned to be completed by alternative analysts.

1) For large studies, a threshold attrition fraction is established (e.g., 50% of all images analyzed by the analyst in question) below which the individual analyst will be eliminated from the study. The criteria are applied on-line during the study. This requires that X percentage of the study is complete the appropriately assess the contribution of the individual analyst. For example, if after 25% study completion, analyst A has failed to meet criteria on >50% of his attempts, then the analyst will be eliminated from the study and the study will continue without this analyst. All images completed by the analyst will be removed from the study. In this case, an alternative analyst may be added to the analyst pool since there remains enough time for the analyst to contribute significantly to the study.

Business Methods

The scope of the invention described herein includes business methods. In some embodiments, the platforms, systems, media, and methods described herein are utilized to offer collaboration models and services on a fee-for-service basis. In further embodiments, the services offered include use of a high-content, high throughput or semi-high throughput anatomical image analysis platform. In still further embodiments, the services are used for preclinical drug discovery, including efficacy and safety evaluation. In a particular embodiment, the services include dendritic spine image analysis useful in CNS drug discovery.

In some embodiments, the business methods contemplated herein include compensating human image analysts for evaluating images. In further embodiments, the image analysts are paid per image analyzed. In other embodiments, the image analysts are paid per unit time spent analyzing images. In other embodiments, the image analysts are paid per analytical action performed within the image analysis application (or time accumulated performing said actions). In particular embodiments, the compensation of an image analyst is adjusted to account for aberrant observations, interpretations, markings, and/or measurements made by the analyst with regard to a particular image or set of images.

Digital Processing Device

In some embodiments, the platforms, systems, media, and methods described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-in

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of image and scoring information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A computer-based platform comprising:
 a. a plurality of computers, each computer configured to provide an image analyst application, the application adapted for and operated by a human image analyst, the human image analyst a non-expert, not selected for a particular expertise or training, the application comprising:
  i. a software module configured to receive an anatomical image;
  ii. a software module configured to provide an interface for the non-expert human image analyst to identify and mark a morphological feature of the image, the marking comprising making a quantitative measurement of the morphological feature;
 b. a server configured to provide a management application comprising:
  i. a software module configured to distribute the anatomical image to a plurality of the image analyst applications;
  ii. a software module configured to receive marked images from the analyst applications and calculate a score for each image, the score based on the marking; and
  iii. a software module configured to statistically compare the scores to identify aberrant non-expert image analyst practices or non-expert image interpretations.

2. The platform of claim 1, wherein the anatomical image is distributed to about 2, 3, 4, 5, 6, 7, 8, 9, or 10 image analyst applications.

3. The platform of claim 1, wherein the anatomical image is a three-dimensional or four-dimensional image.

4. The platform of claim 1, wherein the anatomical image is a histopathology image.

5. The platform of claim 1, wherein the anatomical image is of a neural sample.

6. The platform of claim 1, wherein the anatomical image is a confocal micrograph.

7. The platform of claim 1, wherein the morphological feature is a feature of a dendrite or a dendritic spine.

8. The platform of claim 1, wherein the measurement comprises a density, a diameter, a length, or a combination thereof.

9. The platform of claim 1, wherein the measurement comprises a dendritic spine density, a dendritic spine head diameter, a dendritic spine length, a dendritic spine neck diameter, a dendritic spine distance from a dendrite soma, a dendrite diameter, or a combination thereof.

10. The platform of claim 1, wherein the score is used for diagnosis of medical conditions or evaluation of pharmacological therapies.

11. A computer-implemented system comprising:
 a. a digital processing device comprising an operating system configured to perform executable instructions and a memory device;
 b. a computer program including instructions executable by the digital processing device to create a distributed image analysis application, the application adapted for and operated by a human image analyst, the human image analyst a non-expert, not selected for a particular expertise or training, the application comprising:
  i. a software module configured to receive a two-, three-, or four-dimensional anatomical image from a centralized server, the anatomical image provided to a plurality of image analysis applications;
  ii. a software module configured to provide an interface for the non-expert human image analyst to view the image in three-dimensions, the interface comprising tools for manipulating the image in X, Y, and Z axes, and time progression;
  iii. a software module configured to provide an interface for the non-expert human image analyst to identify and mark a morphological feature of the image, the marking comprising making a quantitative measurement of the morphological feature;
  iv. a software module configured to provide an interface for the non-expert human image analyst to identify and mark a morphological sub-feature of the image, the marking comprising making a quantitative measurement of the morphological sub-feature; and
  v. a software module configured to transmit the marked image to the centralized server.

12. The system of claim 11, wherein the anatomical image is distributed to about 2, 3, 4, 5, 6, 7, 8, 9, or 10 image analyst applications.

13. The system of claim 11, wherein the anatomical image is a histopathology image.

14. The system of claim 11, wherein the anatomical image is of a neural sample.

15. The system of claim 11, wherein the anatomical image is a confocal micrograph.

16. The system of claim 11, wherein the measurement comprises a density, a diameter, a length, or a combination thereof.

17. The system of claim 11, wherein the morphological feature is a feature of a dendrite and the morphological sub-feature is a feature of a dendritic spine.

18. The system of claim 11, wherein the measurement comprises a dendritic spine density, a dendritic spine head diameter, a dendritic spine length, a dendritic spine neck diameter, a dendritic spine distance from a dendrite soma, a dendrite diameter, or a combination thereof.

19. A computer-implemented system comprising:
  a. a digital processing device comprising an operating system configured to perform executable instructions and a memory device;
  b. a computer program including instructions executable by the digital processing device to create a server application comprising:
    i. a software module configured to distribute an anatomical image to a plurality of image analyst applications, each image analyst application adapted for and operated by a human image analyst, the human image analyst a non-expert, not selected for a particular expertise or training;
    ii. a software module configured to receive the anatomical image from the plurality of analyst applications, the received images marked by the non-expert image analyst to identify a morphological feature of the image, the marking comprising a quantitative measurement of the morphological feature;
    iii. a software module configured to calculate a score for each image, the score based on the marking; and
    iv. a software module configured to statistically compare the scores to identify aberrant non-expert image analyst practices or non-expert image interpretations.

20. The system of claim 19, wherein the anatomical image is distributed to about 2, 3, 4, 5, 6, 7, 8, 9, or 10 image analyst applications.

21. The system of claim 19, wherein the anatomical image is a three-dimensional or four-dimensional image.

22. The system of claim 19, wherein the anatomical image is a histopathology image.

23. The system of claim 19, wherein the anatomical image is of a neural sample.

24. The system of claim 19, wherein the anatomical image is a confocal micrograph.

25. The system of claim 19, wherein the measurement comprises a density, a diameter, a length, or a combination thereof.

26. The system of claim 19, wherein the morphological feature is a feature of a dendrite and the morphological sub-feature is a feature of a dendritic spine.

27. The system of claim 19, wherein the measurement comprises a dendritic spine density, a dendritic spine head diameter, a dendritic spine length, a dendritic spine neck diameter, a dendritic spine distance from a dendrite soma, a dendrite diameter, or a combination thereof.

28. A computer-based platform comprising:
  a. a plurality of computers, each computer configured to provide an image analyst application, the application adapted for and operated by a human image analyst, the human image analyst a non-expert, not selected for a particular expertise or training, the application comprising:
    i. a software module configured to receive an image from a centralized server;
    ii. a software module configured to provide an interface for the non-expert human image analyst to identify and mark a feature of the image, the marking comprising making a quantitative measurement of the feature;
  b. a server configured to provide a management application comprising:
    i. a software module configured to distribute the image to a plurality of the image analyst applications;
    ii. a software module configured to receive marked images from the analyst applications and calculate a score for each image, the score based on the marking; and
    iii. a software module configured to statistically compare the scores to identify aberrant non-expert image analyst practices or non-expert image interpretations.

29. The platform of claim 28, wherein the measurement comprises a density, a diameter, a length, a distance, an area, or a combination thereof.

* * * * *